United States Patent [19]

Baker et al.

[11] Patent Number: 5,670,679

[45] Date of Patent: Sep. 23, 1997

[54] PROCESS FOR THE MANUFACTURING OF SELECTED HALOGENATED HYDROCARBONS CONTAINING FLUORINE AND HYDROGEN AND COMPOSITIONS PROVIDED THEREIN

[75] Inventors: Ralph Thomas Baker, Wilmington; Richard Paul Beatty, Newark; William Brown Farnham, Hockessin, all of Del.; Robert Lewis Wallace, Jr., Aston, Pa.

[73] Assignee: E. I. Du Pont de Nemours and Company, Wilmington, Del.

[21] Appl. No.: 458,784

[22] Filed: Jun. 2, 1995

Related U.S. Application Data

[62] Division of Ser. No. 315,025, Sep. 29, 1994, Pat. No. 5,545,769.

[51] Int. Cl.$^6$ ............................ C07F 15/04; C07F 9/02
[52] U.S. Cl. ........................ 556/18; 556/21; 556/13; 556/30; 556/140; 556/146; 546/2
[58] Field of Search ................... 556/140, 146, 556/18, 21, 30, 13; 546/2

[56] References Cited

U.S. PATENT DOCUMENTS

| | | | |
|---|---|---|---|
| 3,496,217 | 2/1970 | Drinkard, Jr. et al. | 260/465.8 |
| 3,496,218 | 2/1970 | Drinkard, Jr. | 260/465.8 |
| 3,631,191 | 12/1971 | Kane et al. | 260/439 R |
| 3,846,461 | 11/1974 | Shook, Jr. | 260/439 R |
| 3,847,959 | 11/1974 | Shook, Jr. et al. | 260/439 R |
| 3,881,949 | 5/1975 | Brock | 134/31 |
| 3,903,120 | 9/1975 | Shook, Jr. et al. | 260/439 R |
| 4,715,900 | 12/1987 | Connon et al. | 134/31 |
| 5,059,728 | 10/1991 | Li et al. | 570/134 |
| 5,171,902 | 12/1992 | Krespan et al. | 570/175 |
| 5,194,170 | 3/1993 | Merchant et al. | 252/67 |
| 5,221,493 | 6/1993 | Merchant et al. | 252/67 |
| 5,250,208 | 10/1993 | Merchant et al. | 252/67 |
| 5,300,712 | 4/1994 | Baker | 570/176 |

FOREIGN PATENT DOCUMENTS

WO92/06941 4/1992 WIPO.
WO95/19947 7/1995 WIPO.

OTHER PUBLICATIONS

Collman, J.P., "2.2 Bonding iin Organotransition Metal Complexes", *Principles and Applications of Organotransition Metal Chemistry*, University Science Books, Mill Valley, CA, pp. 37–43 (1987).
Cundy, C.S. et al, "Reactions of Low–valent Metal Complexes with Fluorocarbons. Part XII. Fluoro–olefin Reactions of Zerovalent Nickel Complexes", *J. Chem. Soc. (A)*, 1647–1653 (1970).
Maples, P.K. et al, "Reactions of Low–valent Metal Complexes with Fluorocarbons. Part XXVI. 1,1,1–Tris(diphenylphosphinomethyl)– and 1,1,1–Tris(diphenylarsinomethyl)–ethane", *J. Chem. Soc. Dalton Transactions*, 388–392 (1973).

Green, M. et al, "Reactions of Low–valent Metal Complexes with Fluorocarbons. Part XVIII t–Butyl Isocyanide–Nickel Complexes", *J. Chem. Soc. (A)*, 2828–2834 (1971).
Tolman, C.A. et al, "Olefin Complexes of Nickel(O). II. Preparation and Properties of (Olefin)bis(tri–o–tolyl phosphite(nickel Complexes", *J. Am. Chem. Soc.*, 96(9), 2774–2780 (May 1, 1974).
Watterson, K. F. et al, "Perfluoroolefin–Transition Metal Complexes", *Chemsitry and Industry*, 991 (1959).
Manuel, T.A., "Some Tertiary Phosphine–Iron Carbonyl Compounds", *Inorganic Chemistry*, 2, 854–858 (1963).
Fields, R. et al, "Mono(fluoroolefin) Complexes of Pentacarbonyliron", *Chemical Communications*, 243 (1967).
Coyle, T.D. et al, "A novel heterocyclic cobalt compound", *J. Inorganic Nuclear Chemistry*, 20, 172 (1961).
Stone, F.G.A. et al, "Reactions of Low–valent Metal Complexes with Fluorocarbons. Part XV. Acetylacetonatobis(methyldiphenyl– or triphenyl–phosphine)rhodium", *J. Chem. Soc. Sect. A*, 3166 (1970).
Browning, J. et al, "Reactions of Low–valent Metal Complexes with Fluorocarbons. Part XXV. Phosphine, Phosphite and Cyclo–octa–1,5–diene Platinum Complexes", *J. Chem. Soc. Dalton Transactions*, 381 (1973).
Green, M. et al, "Reaction of Fluoroolefins with Iron and Ruthenium Carbonyl Complexes", *J. Chem. Soc. Sect. A*, 2975–2981 (1970).
Seidel, W.C. et al, "Ethylene[bis(tri–o–tolyl phosphite)] nickel(0)", *Inorg. Chem.*, 9(10), 2354–2357 (1970).
Ittel, S.D., "34. Olefin, Acetylene, Phosphine, Isocyanide, and Diazene Complexes of Nickel(0)", *Inorg. Synthesis*, 17, 117–124 (1977).

(List continued on next page.)

*Primary Examiner*—Porfirio Nazario-Gonzalez

[57] ABSTRACT

A process is disclosed for the manufacture of product compounds of the formula $HC(R^1)_2C(R^1)_2C(R^2)_2C(R^2)_2H$ wherein each $R^1$ is independently selected from the group consisting of H, F, Cl, CN, R, OR, $CO_2R$, C(O)R, OC(O)R, $R^f$, $OR^f$, $CO_2R^f$ $C(O)R^f$ and $OC(O)R^f$ where R is a hydrocarbyl group and $R^f$ is a $C_1$ to $C_{10}$ polyfluoroalkyl group, provided that at least one $R^1$ is F, and wherein each $R^2$ is independently selected from the group consisting of H, F, Cl, CN, R, OR, $CO_2R$, C(O)R, OC(O)R, $R^f$, $OR^f$, $CO_2R^f$, $C(O)R^f$, $OC(O)R^f$ and difunctional linkages where an $R^2$ group on each of two adjacent carbon atoms together form a link selected from the group consisting of —$CH_2CH_2CH_2$—, —$CH_2CH_2CH_2CH_2$—, —$CH_2CH_2CH$ ($CH_3$—, —$CH_2CH(CH_3)CH_2$—, —C(O)OC(O)—, and norborndiyl. The process involves reacting a metallacycle of the formula $L_mM(1,4-C(R^1)_2C(R^1)_2C(R^2)_2C(R^2)_2—)$ wherein $R^1$ and $R^2$ are as defined above, and wherein M is a metal selected from the group consisting of Group 8, Group 9 and Group 10 metals, each L is a ligand selected from the group consisting of Group 14, Group 15 and Group 16 ligands, and m is an integer from 1 to 4, in the liquid phase with hydrogen. Also disclosed are certain compositions comprising product compounds within the above product compound formula and certain metallacycle compounds within the above metallacycle formula.

12 Claims, No Drawings

OTHER PUBLICATIONS

Ittel, S.D., "26. Complexes of Nickel(0)", *Inorg. Synthesis*, 28, 98–104 (1990).

Stockis, A. et al, "Metallacyclopentanes and Bisolefin Complexes", *J. Am. Chem. Soc.*, 102(9), 2952–2962 (1980).

Schröder, W. et al, *J. of Organometallic Chemistry*, 408, C25–C29 (1991).

Burch, R.R. et al, *Organometallics*, 7, 1642–1648 (1988).

Davies, C.H. et al, *J. of the Chemical Society, Dalton Translations*, pp. 357–363 (1974).

Browning, J. et al, *J. of the Chemical Society, Section A: Inorganic Physical and Theoretical Chemistry*, Letchworth GB, pp. 453–457 (1991).

Haszeldine, R.N. et al, *J. of the Chemical Society, Perkin Transactions 1*, Letchworth GB, pp. 1943–1947 (1979).

Burdon, J. et al, *J. of Fluorine Chemistry*, 40, 283–318 (1988).

Collman, J.P. et al., *Principles and Applications of Organotransition Metal Chemistry* (University Science Books, Mill Valley), pp. 292–293 (1987).

Chappell, S.D. et al. *Polyhedron* 1, 739–777 (1982).

5,670,679

1

PROCESS FOR THE MANUFACTURING OF SELECTED HALOGENATED HYDROCARBONS CONTAINING FLUORINE AND HYDROGEN AND COMPOSITIONS PROVIDED THEREIN

This is a division of application Ser. No. 08/315,025, filed Sep. 29, 1994, now U.S. Pat. No. 5,545,769.

FIELD OF THE INVENTION

This invention relates to liquid phase processes for producing selected halogenated hydrocarbons containing fluorine, and more particularly to processes involving hydrogenolysis for producing halogenated hydrocarbons containing fluorine and hydrogen and compositions provided in such processes.

BACKGROUND OF THE INVENTION

Chlorofluorocarbons (CFCs, i.e., compounds containing only carbon, fluorine and chlorine) have been used for many years as refrigerants, heat transfer media, foam expansion agents, aerosol propellants, solvents and power cycle working fluids. For example, various CFC solvents have been used as cleaning liquids for the removal of contaminants from contaminated articles and materials. Certain fluorine-containing organic compounds such as 1,1,2-trichloro-1,2,2-trifluoroethane (CFC-113) have been reported as useful for this purpose, particularly with regard to cleaning organic polymers and plastics which may be sensitive to other more common and more powerful solvents such as trichloroethylene or perchloroethylene. Recently, however, there have been efforts to reduce the use of certain compounds such as trichlorotrifluoroethane which also contain chlorine because of a concern over their potential to deplete ozone, and to thereby affect the layer of ozone that is considered important in protecting the earth's surface from ultraviolet radiation. Consequently, there is a worldwide effort to find alternative compounds which contain fewer or preferably no chlorine substituents.

Boiling point, flammability and solvent power can often be adjusted by preparing mixtures of solvents. For example, certain mixtures of 1,1,2-trichloro-1,2,2-trifluoroethane with other solvents (e.g., isopropanol and nitromethane) have been reported as useful in removing contaminants which are not removed by 1,1,2-trichloro-1,2,2-trifluoroethane alone, and in cleaning articles such as electronic circuit boards where the requirements for a cleaning solvent are relatively stringent (i.e., it is generally desirable in circuit board cleaning to use solvents which have low boiling points, are non-flammable, have low toxicity, and have high solvent power so that flux such as rosin and flux residues which result from soldering electronic components to the circuit board can be removed without damage to the circuit board substrate).

While boiling point, flammability, and solvent power can often be adjusted by preparing mixtures of solvents, the utility of the resulting mixtures can be limited for certain applications because the mixtures fractionate to an undesirable degree during use. Mixtures can also fractionate during recovery, making it more difficult to recover a solvent mixture with the original composition. Azeotropic compositions, with their constant boiling and constant composition characteristics, are thus considered particularly useful.

The properties of halogenated hydrocarbons can be influenced by the arrangement of the halogens (and hydrogen,

2 when present) on the carbon framework. One of the challenges in preparing compounds containing fluorine and hydrogen has been achieving the desired arrangement of such substituents.

One arrangement involves providing a hydrogen on different carbons spaced a selected distance from one another along a carbon chain. For example, it can be desirable to provide a hydrogen substituent on each of two carbon atoms which are separated from one another by a chain of two other carbon atoms. 1,1,2,2,3,3,4,4-Octafluorobutane (HFC-338pcc) is such a compound. HFC-338pcc forms useful blends, and particularly azeotropes, with solvents such as alcohols, ketones, and other halogenated solvents to form compositions useful for cleaning surfaces, especially electronic components as disclosed in U.S. Pat. Nos. 5,250,208, 5,221,493, and 5,194,170. There is a need for non-chlorinated solvents like HFC-338pcc (which have little effect on the ozone layer) as replacements for more chlorinated solvents such as CFC-113. There is also a need for processes for effectively producing compounds such as HFC-338pcc.

A few classes of fluorinated metallacycles have been reported, but little has been disclosed about the chemistry of this uncommon type of compounds. Certain five-membered ring metallacycles containing a dimerized tetrafluoroethylene group (i.e., $-(CF_2)_4-$) bound to Fe, Ni, Ru, Co, Rh and Pt have been disclosed. These include complexes of the type $(ligand)_4Fe(1,4-CF_2CF_2CF_2CF_2-)$ and $(ligand)_4Ru(1,4-CF_2CF_2CF_2CF_2-)$ where the ligand is CO, phosphine, phosphite, or a N-donor ligand, as reported by Watterson, et al. in *Chemistry and Industry* page 991 (1959), Manuel in *Inorganic Chemistry* Vol. 2, page 854 (1963), and Fields et al. in *Chemical Communications* page 243 (1967); complexes of the type $Ni(ligand)_2(1,4-CF_2CF_2CF_2CF_2-)$ where the ligand is a phosphorus donor ligand, diolefin, or isocyanide, as reported by Maples et al., *J. Chemical Society, Dalton Transactions* page 388 (1973), by Cundy et al., *J. Chemical Society Sect. A* page 1647 (1970), and by Tolman et al., *J. American Chemical Society*, Vol. 96, page 2774 (1974); as well as the individual complexes $Co(\eta^5-C_5H_5)(CO)(1,4-CF_2CF_2CF_2CF_2-)$ reported by Coyle et al., *J. Inorganic Nuclear Chemistry* Vol. 20 page 172 (1961), $Rh(acetylacetonate)(PMe_2Ph)_2(1,4-CF_2CF_2CF_2CF_2-)$ reported by Stone et al., *J. Chemical Society Sect. A* page 3166 (1970), and $Pt(\eta^2,\eta^2-1,5-cyclooctadiene)(1,4-CF_2CF_2CF_2CF_2-)$ reported by Browning et al., *J. Chemical Society, Dalton Transactions* page 381 (1973). Five-membered ring metallacycles containing a $-CHF(CF_2)_2CHF-$ group bound to Fe have also been reported by Green et al., *J. Chemical Society Sect. A* page 2975 (1970).

SUMMARY OF THE INVENTION

This invention provides a process for the manufacture of a product compound of the formula $HC(R^1)_2C(R^1)_2C(R^2)_2C(R^2)_2H$ wherein each $R^1$ is independently selected from the group consisting of H, F, Cl, CN, R, OR, $CO_2R$, $C(O)R$, $OC(O)R$, $R^f$, $OR^f$, $CO_2R^f$ $C(O)R^f$ and $OC(O)R^f$, where R is a hydrocarbyl group and $R^f$ is a $C_1$ to $C_{10}$ polyfluoroalkyl group, provided that at least one $R^1$ is F, and wherein each $R^2$ is independently selected from the group consisting of H, F, Cl, CN, R, OR, $CO_2R$, $C(O)R$, $OC(O)R$, $R^f$, $OR^f$, $CO_2R^fC(O)R^f$, $OC(O)R^f$ and difunctional linkages where an $R^2$ on each of two adjacent carbon atoms together form a link selected from the group consisting of $-CH_2CH_2CH_2-$, $-CH_2CH_2CH_2CH_2-$, $-CH_2CH_2CH(CH_3)-$, $-CH_2CH(CH_3)CH_2-$, $-C(O)OC(O)-$, and norborndiyl. The process comprises reacting a metallacycle of the formula

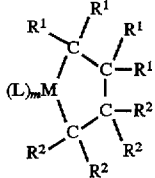

(i.e., $L_mM(1,4-C(R^1)_2C(R^1)_2C(R^2)_2C(R^2)_2-))$ wherein $R^1$ and $R^2$ are as defined above, and wherein M is a metal selected from the group consisting of Group 8, Group 9 and Group 10 metals, each L is a ligand selected from the group consisting of Group 14, Group 15 and Group 16 ligands, and m is an integer from 1 to 4, in the liquid phase with hydrogen.

This invention also provides metallacyclic compounds, for example, a compound of the formula $L_2Ni(1,4-CR^1{}_2CR^1{}_2CR^2{}_2CR^2{}_2-)$ wherein L, $R^1$ and $R^2$ are as defined above, provided that when each L is a Group 15 ligand, and each $R^1$ and $R^2$ is F, then L is not trimethylphosphite, tri-o-tolylphosphite, triethylphosphine, tributylphosphine, methyldiphenyl phosphine, triphenylphosphine, dimethylphenyl arsine, 4-methylpyridine, dimethylarsine, 2,2-bipyridyl, or 1,2-bis (diphenyl phosphino)ethane, and provided that when three $R^1$ groups and three $R^2$ groups are F and the remaining $R^1$ group and $R^2$ group are H, then L is not triphenylphosphine or methydiphenylphosphine.

This invention also provides compositions comprising a compound of the formula $HCFR^1CFR^1CHR^2CH_2{}^{R2}$ wherein each $R^1$ is selected from the group consisting of H, Cl, F, CN, and $OCF_3$ and each $R^2$ is as defined above, provided that at least one $R^1$ is F.

DETAILED DESCRIPTION

A metallacycle is a cyclic carbon compound where one or more carbons are replaced by a transition metal. Applicants have discovered that certain fluorine-containing metallacycles can be reacted with hydrogen to add hydrogen to each of two carbon atoms separated from one another by a chain of two other carbon atoms and produce selected halogenated hydrocarbons containing fluorine and hydrogen.

An olefinic compound of the formula $(R^1)_2C=C(R^1)_2$ and another or the same olefinic compound of the formula $(R^2)_2C=C(R^2)_2$ may be reacted in the liquid phase with a metal complex, soluble in the liquid phase, of the formula $M_xL_n$, where x is an integer from 1 to 3 and n is an integer from 1 to 12 to form a metallacycle of the structure shown in the Summary of the Invention. In accordance with this invention, the metallacycle may be reacted in the liquid phase with hydrogen to produce an organic compound of the formula, $HC(R^1)_2C(R^1)_2C(R^2)_2C(R^2)_2H$. The metal fragment $ML_m$ released by the hydrogenation reaction, which under the reaction conditions may revert partly or completely to $M_xL_n$, typically may be converted back to the metallacyclic compound, $ML_m(1,4-C(R^1)_2C(R^1)_2C(R^2)_2C(R^2)_2-)$, by subsequent reaction with the olefinic compounds $(R^1)_2C=C(R^1)_2$ and $(R^2)_2C=C(R^2)_2$. Each $R^1$ and $R^2$ may be independently selected from the group consisting of H, F, Cl, CN, OR, $CO_2R$, C(O)R, OC(O)R, R', OR', $CO_2R'$, C(O)R', and OC(O)R', (provided that at least one $R^1$ is F). Also, one $R^2$ group on each of two adjacent carbons may together form a link selected from the group consisting of $-CH_2CH_2CH_2-$, $-CH_2CH_2CH_2CH_2-$, $-CH_2CH_2CH(CH_3)-$, $CH_2CH(CH_3)CH_2-$, $-C(O)OC(O)-$, and norborndiyl (i.e.,

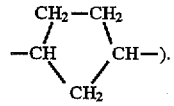

R is a hydrocarbyl group. By hydrocarbyl is meant a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Examples of hydrocarbyl groups include, for example, methyl, ethyl, propyl, isopropyl, butyl, isobutyl, t-butyl, cyclopropyl, cyclobutyl, cyclopentyl, methylcyclopentyl, cyclohexyl, methylcyclohexyl, benzyl, phenyl, o-tolyl, m-tolyl, p-tolyl, xylyl, vinyl, allyl, butenyl, cyclohexenyl, cyclooctenyl, cyclooctadienyl, and butynyl. $R_f$ is a polyfluoroalkyl group having from 1 to 10 carbon atoms. Examples of suitable polyfluoroalkyl groups include, for example, $-CH_2F$, $-CHF_2$, $-CF_3$, $-CH_2CF_3$, $-CF_2CHF_2$, $-C_2F_5$, $-CH_2CF_2CHF_2$, $-CH_2C_2F_5$, $-CH_2CH_2C_2F_5$, $-CF_2CHFCF_3$, $-CF_2CF_2CHF_2$, $-CH_2CF_2CF_2CF_2CHF_2$, $-CF_2CF_2CF_2CF_3$, and $-CH_2CH_2CF_2CF_2CF_2CF_3$. Preferably each $R^1$ is selected from the group H, Cl, F, CN, and $OCF_3$ (provided, as noted above, that at least one $R^1$ is F). Of note are embodiments where at least two $R^1$ groups are F and embodiments where at least three of the $R^1$ groups are selected from Cl or F. Preferably each $R^2$ is independently selected from the group H, Cl, F, CN, $OCF_3$, $C_6H_5$, $CF_3$ and $CO_2CH_3$.

Examples of olefins of the formula $(R^1)_2C=C(R^1)_2$ include, $CF_2=CF_2$, $CF_2=CFCl$, $CF_2=CCl_2$, $CFCl=CFCl$, $CFCl=CCl_2$, $CF_2=CFH$, $CF_2=CH_2$, $CFH=CFH$, $CFH=CH_2$, $CF_2=CF(CN)$, $CF_2=C(CN)_2$, $CF(CN)=CF(CN)$, $CF(CN)=C(CN)_2$, $CF_2=CFCF_3$, $CF_2=CHCF_3$, $CF_2=CFCF_2CF_3$, $CF_2=CFCF_2CF_2CF_3$, $CF_2=CFCH_3$, $CF_2=CF(C_6H_5)$, $CF_2=CF(C_6F_5)$, $CF_2=CFOCH_3$, $CF_2=CFOCH_2F$, $CF_2=CFOCHF_2$, $CF_2=CFOCF_3$, $CF_2=CHOCF_2CHF_2$, $CF_2=CFOCF_2CF_2CF_3$, $CF_2=CFCO_2CH_2CH_3$, and $CF_2=CFCO_2CF_2CF_3$. Examples of olefins of the formula $(R^2)_2C=C(R^2)_2$ include those exemplified for the formula $(R^1)_2C=C(R^1)_2$, as well as $CH_2=CH_2$, $CH_2=CHCH_3$, $CH_2=CHCF_3$, $CH_2=CHCH_2CH_3$, $CH_2=CHCF_2CF_3$, $CH_2=CHOCH_3$, $CH_2=CHOCF_3$, $CH_2=CHOC(O)CH_3$, $CH_2=CHOC(O)CF_3$, $CH_2=CHCO_2CH_3$, $CH_2=CHCO_2CF_3$, $H_3CO_2CCH=CHCO_2CH_3$, $CH_2=CHCl$, $CH_2=CCl_2$, $CHCl=CHCl$, $CHCl=CCl_2$, $CH_2=CHCF_3$, $CH_2=CHOCF_3$, $CH_2=CHC_6H_5$, $CH_2=CHCl$, $CH_2=CHF$, $CH_2=CH(CN)$, $CH(CN)=CH(CN)$, $HC(CN)=CHCH_2CH_2CN$, cyclopentene, methylcyclopentenes, cyclohexene, norbornene, and maleic anhydride. Preferred olefins of the formula $(R^1)_2C=C(R^1)_2$ include $CF_2=CF_2$, $CF_2=CFCl$, $CF_2=CFH$, $CF_2=CF(CN)$, $CF_2=CFOCF_3$, and $CF_2=CFCO_2CF_2CF_3$. Preferred olefins of the formula $(R^2)_2C=C(R^2)_2$ include those preferred for the formula $(R^1)_2C=C(R^1)_2$, as well as, $CH_2=C_2$, $CH_2=CHCF_3$, $CH_2=CHOCF_3$, $CH_2=CHC_6H_5$, $CH_2=CHF$, $CH_2=CHCl$, $CH_2=CHCN$, and $CH_2=CHCO_2CH_3$. Of note are embodiments wherein each $R^1$ and $R^2$ is either H or F. Also of note are embodiments where the first olefinic reactant is the same as the second olefinic reactant (e.g., both are $CF_2=CF_2$). Especially preferred for the process of this invention is $CF_2=CF_2$.

The metals useful in this invention to prepare metallacycles include those of Periodic Table Groups 8 to 10.

Periodic Table Group includes those elements organized in Groups described as the "new notation" in the Periodic Table appearing in the CRC Handbook of Chemistry and Physics, 67th Edition, CRC Press (1986–1987). The metals are selected from Fe, Co, Ni, Ru, Rh, Pd, Os, Ir and Pt. Preferred metals include Fe, Co, Rh, Ru, Pt and Ni. Especially preferred are metallacycles of Ni.

The ligands useful in forming the metal complexes and metallacycles may be defined as any atoms or molecules capable of functioning as electron donors. Generally, preferred ligands are capable of functioning also as pi-acceptors or pi-acids. A description of such ligands may be found in "Principles and Applications of Organotransition Metal Chemistry" by J. P. Collman et al., published by University Science Books, 1987; particularly on pages 37–43.

The ligands useful in this invention to prepare metallacycles include those where the elements bonded to the metal are selected from those of Periodic Table Groups 14 to 16. These are referred to herein as Group 14, Group 15 and Group 16 ligands. That is, the elements of these ligands bound to the metal of the metallacycle are selected from the group consisting of C, Si, Ge, Sn, Pb, N, P, As, Sb, Bi, O, S, Se and Te. Of note are Group 14 ligands such as CO (carbon monoxide), hydrocarbyl isocyanides (CNR), $\eta^2$ olefinic ligands such as ethylene or 1,5-cyclooctadiene, $\eta^2$ alkyne ligands such as acetylene, diphenyl acetylene, or hexafluoro-2-butyne, $\eta^5$-$C_5R''_5$ ligands where R" is hydrocarbyl or hydrogen such as the cyclopentadienide ligand (i.e., R" is H), and $\eta^3$-$C_3R''_3$ ligands such as the allyl ligand (i.e., R" is H).

Also of note are Group 15 ligands including mono-, bi-, or polydentate neutral ligands such as pyridine, picoline, 2,2'-bipyridine, ethylene diamine, and hydrocarbyl nitriles such as acetonitrile or benzonitrile. Included in group 15 ligands are mono-, bi-, or polydentate anionic ligands such as dihydrocarbyl amides such as $N(CH_3)_2$ and dipyrazolylborates such as $(CH_3)_2B(N_2C_3H_3)_2$. Especially useful are mono- or bidentate group 15 ligands of the formula $E^1(R^3)_3$ or $(R^3)_2E^1R'E^1(R^3)_2$ wherein $E^1$ is selected from the group consisting of N, P, As, Sb, and Bi, $R^3$ is selected from the group consisting of H, R, OR, OH, $NH_2$, NHR and $NR_2$ where each R is a hydrocarbyl group, and R' is an ether, alkylene, or arylene link between $E^1$ atoms. In addition, R' may incorporate various pendant functional groups such as OR, OH, $NH_2$, NHR and $NR_2$. Examples of R' include —$CH_2CH_2$—, —$CH_2CH_2CH_2CH_2$—, —$C_6H_4$—, —O—, —$OC_6H_4$—$C_6H_4O$—, and —$CH_2CH_2OCH_2CH_2$—. In some embodiments of these ligands two or more R and/or $R^3$ groups may be cojoined. Examples of Group 15 ligands include bidentate ligands wherein $E^1$ is P and $R^3$ is selected from the group consisting of alkyl or aryl and R' is —$CH_2CH_2$— or $CH_2CH_2CH_2CH_2$—, including, for example, $(C_6H_5)_2PCH_2CH_2P(C_6H_5)_2$, $(CH_3)_2PCH_2CH_2P(CH_3)_2$, and $(C_6H_5)_2PCH_2CH_2CH_2CH_2P(C_6H_5)_2$ (herein referred to as DPPB). Also included are monodentate and bidentate phosphites, phosphinites, and phosphonites $(R^4)_2PR'P(R^4)_2$, where each $R^4$ is independently R or OR, where R is a hydrocarbyl group, for example,

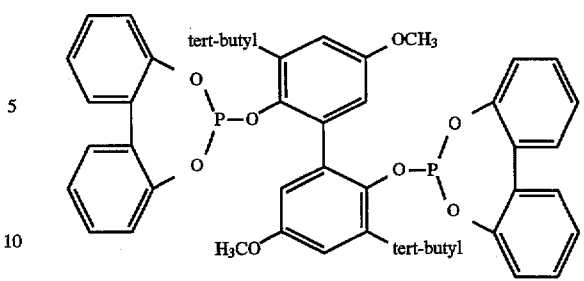

(referred to herein as "diphite").

These ligands may be prepared by a variety of methods known in the art, for example see descriptions in WO 93,03839, U.S. Pat. Nos. 4,769,498, 4,688,651, and J. Amer. Chem. Soc., vol 115, page 2066 (1993). The reaction of 2,2'-biphenol with phosphorus trichloride gives 1,1'-biphenyl-2,2'-diyl phosphorochloridite. The reaction of this chlorodite with 2,2'-dihydroxy-3,3'-di-t-butyl-5,5'-dimethoxy-1,1'-biphenyl in the presence of triethylamine gives the diphite ligand illustrated above. Reaction of the chlorodite with mono-hydroxy compounds such as 2-t-butyl-4-methoxy phenol in the presence of triethylamine gives the monodentate ligand.

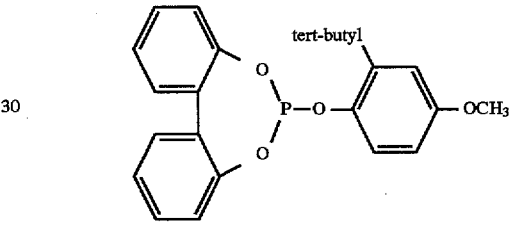

(referred to herein as "monophite").

Preferred examples include monodentate ligands wherein $E^1$ is P and each $R^3$ is independently selected from the group consisting of —$OCH(CH_3)_2$, —$CH_2CH_3$, —$CH_2CH_2CH_2CH_3$, phenyl, and —O—(o,m,p)tolyl. Triisopropyl phosphite is considered especially useful in combination with Ni and $Ni(P(OCH(CH_3)_2)_3)_4$ (i.e., n is 4) is an especially useful metal complex for preparing nickel metallacycles. Of note are embodiments where the metallacycle is reacted with hydrogen in the presence of tri-isopropyl phosphite and the metal complex (e.g., a metal complex of Ni and triisopropyl phosphite) is-produced along with the product compound.

Also of note are monodentate Group 16 ligands of the formula $E^2(R^5)_2$ and bidentate Group 16 ligands of the formula $(R^5)E^2R'E^2(R^5)$, wherein $E^2$ is selected from the group consisting of O, S, Se, and Te, R' is as defined above, and $R^5$ is a hydrocarbyl group. In some embodiments two or more $R^5$ groups may be cojoined. Examples of these ligands include ethers such as tetrahydrofuran or t-butyl methyl ether, and diethers such as 1,2-dimethoxyethane or 2,5-dithiohexane. Included in group 16 ligands are mono-, bi-, or polydentate anionic ligands such as alkoxide, thiolate, nitrate, nitrite, phosphate, sulfate, hydrocarbyl sulfonate, acetylacetonate, dithiocarbamate, and carboxylate.

Also of note are mixed donor ligands containing group 14, 15, and/or 16 donors in the same ligand such as thiocarbamate, 2-pyridyl diphenylphosphine, and β-methoxyethyl dicyclohexylphosphine, which are known in the art.

Metal complexes useful in this invention can have from 1 to 3 metal atoms, and from 1 to 12 ligands (e.g., $Fe_3(CO)_{12}$).

The metallacycle formed from the metal complexes has only one complexes has only one metal atom and typically has from 1 to 4 ligands. For the purposes of this invention multidentate ligands can replace one or more monodentate ligands.

The preferred metal complexes for preparing metallacycles for the process of this invention are generally zero-valent nickel complexes of the type $NiL_4$ or $NiL_3$ where each L may be independently selected from the ligands disclosed above. The $NiL_4$ or $NiL_3$ metal complexes may be pre-formed or prepared in situ from suitable nickel precursors. Preferred $NiL_4$ or $NiL_3$ complexes contain ligands such as CO (carbon monoxide), hydrocarbyl isocyanides such as t-butyl isocyanide, olefinic ligands such as ethylene, or 1,5-cyclooctadiene, alkynes such as acetylene or diphenyl acetylene, hydrocarbyl phosphines, arsines, stibines, phosphites, arsenites, stibites, and mixtures thereof.

An especially preferred group of nickel complexes has the general formula $NiL_4$ or $NiL_3$ where each L is independently selected from those having the formula $P(R^4)_3$ wherein the $R^4$s may be the same or different. If desired any of the $R^4$ groups may be cojoined. Thus the preferred neutral ligands of this group are trihydrocarbyl phosphines such as triphenylphosphine or tributylphosphine, trihydrocarbyl phosphites such as tri(ortho-tolyl)phosphite or triethylphosphite, trihydrocarbyl phosphinites $R_2P(OR)$, and trihydrocarbyl phosphonites $RP(OR)_2$ (where the R groups may be the same or different). An especially preferred ligand is triisopropyl phosphite, $(P(OCH(CH_3)_2)_3)$. Under many of the reaction conditions one or more of L ligands may become disassociated from the nickel.

Zero-valent nickel complexes can be prepared or generated according to techniques well known in the art (see, e.g., U.S. Pat. Nos. 3,496,217, 3,631,191, 3,846,461, 3,847,959, 3,903,120, and Tolman, et al. *J. Am. Chem. Soc.* Vol. 96, page 2774 (1974). Zero-valent nickel compounds that contain ligands which can be displaced by the organophosphorus ligand are a preferred source of zero-valent nickel. Two such preferred zero-valent nickel compounds are $Ni(COD)_2$ (where COD is 1,5-cyclooctadiene) and $Ni(P(O-o-C_6H_4CH_3)_3)_2(C_2H_4)$, both of which are known in the art (see, e.g., Seidel et al., *Inorg. Chem.*, 1970, Vol. 9, p. 2354 and S. D. Ittel, *Inorganic Synthesis*, Vol. 17, 1977, pp. 117–124 and Vol. 28, 1990, pp. 98–104). Alternatively, divalent nickel compounds may be combined with a reducing agent, and are then able to serve as suitable sources of zero-valent nickel in the reaction. Suitable divalent nickel compounds include compounds of formula $NiY_2$, where Y is halide, carboxylate, or acetylacetonate. Suitable reducing agents include metal borohydrides, metal aluminum hydrides, metal alkyls, Zn, Fe, Al Na, or $H_2$. Elemental Ni, preferably nickel powder, when combined with a halogenated catalyst, as described in U.S. Pat. No. 3,903,120, is also a suitable source of zero-valent nickel.

The solvent used for the preparation of the metallacycle and hydrogenolysis of the metallacycles of this invention should be liquid at the reaction temperature and pressure, should not exert any deleterious effect towards the olefinic reactants or the metallacycle, and should have the property of dissolving a sufficient amount of metal complex and metallacycle to react with olefinic compounds and hydrogen, respectively.

Suitable solvents include cyclic or acyclic hydrocarbons (e.g., pentane, cyclopentane, hexanes, cyclohexane, mineral spirits, or kerosene), aromatic hydrocarbons (e.g., benzene, chlorobenzene, toluene, xylene, mesitylene, or tetralin), nitriles (e.g., acetonitrile, valeronitrile, benzonitrile or adiponitrile), ethers (e.g., diethyl ether, methyl t-butyl ether, 1,2-dimethoxyethane, tetrahydrofuran or dioxane), ketones (e.g., acetone), esters (e.g., dimethyl carbonate, methyl acetate or methyl formate) or polar organic solvents (e.g., dimethyl sulfoxide, N,N-dimethyl formamide, pyridine, N-ethyl-morpholine, isopropanol, and sulfolane). Mixtures of the above solvents may also be employed to advantage.

In many cases, the ligand, L, may serve as at least part (i.e., part or all) of the solvent (see Example 19). The presence of ligand during hydrogenolysis may be particularly advantageous in stabilizing the metal fragment liberated as a result of hydrogenolysis of the metallacycle. In other cases, the olefin, $(R^2)_2C=C(R^2)_2$, may serve as at least part (i.e., part or all) of the solvent. Of note are embodiments wherein the solvent is the product of the hydrogenolysis of the metallacycle, $HC(R^1)_2C(R^1)_2C(R^2)_2C(R^2)_2H$ (e.g., 1,1,2,2,3,3,4,4-octafluorobutane).

In one embodiment of this invention the metallacycle is prepared in a separate step by contacting a metal complex of the type $M_xL_n$ dissolved in a suitable solvent, as defined above, with an olefinic compound of the formula $(R^2)_2C=C(R^2)_2$ and another or the same olefinic compound of the formula $(R^1)_2C=C(R^1)_2$, where $R^1$ and $R^2$ are as defined above. Typically, the reaction is accomplished at temperatures from −25° to 200° C., at pressures of about 5 kPa (about 0.05 atm.) to 10,000 kPa (about 100 atm.) and at a contact time of about 1 minute to 24 hours to form a metallacycle, $L_mM(1,4-C(R^1)_2C(R^1)_2C(R^2)_2C(R^2)_2—)$. When $(R^2)_2C=C(R^2)_2$ and $(R^1)_2C=C(R^1)_2$ are different alkenes, their preferred mole ratio is normally from about 0.01:1 to 100:1. The mole ratio of alkene to metal employed may vary over a wide range (e.g., from about 0.1:1 to about 100:1). The preferred ratio is normally from about 1:1 to 10:1, but depends to some extent on the particular metal complex and alkene(s) employed, and the desired rate and conversion of $M_xL_n$ to metallacycle. Theoretically, a mole ratio of 2 alkenes per metal is required to achieve complete conversion of $M_xL_n$ to the metallacycle. It may be desirable to use mole ratios greater than 2 to decrease the time required for metallacycle formation or to ensure complete conversion of the limiting reagent, $M_xL_n$, to metallacycle. The excess alkene or its hydrogenation product may then be recovered for recycle or disposal. To avoid this recovery step, it may be desirable to reduce the amount of excess alkene employed to less than 2 per metal, so that the alkene is the limiting reagent and is completely consumed. This results in less than complete conversion of $M_xL_n$ to metallacycle, but avoids the presence of excess alkene in the metallacycle product. The exact temperature which is preferred is dependent to a certain extent on the particular metal complex and alkenes being used and the desired rate. Low temperatures may be used, but require relatively long reaction times for practical conversion. Higher temperatures dramatically increase rate, but may in certain cases increase formation of byproducts, which decreases yield. Similarly, low pressures (e.g., about 100 to 200 kPa) are often satisfactory for carrying out the present invention, but moderate pressures (e.g., 200 to 1000 kPa) can be used to increase reaction rate if desired for economic reasons. Pressures higher than 1000 kPa (about 10 atm.) may be employed if desired, but may often be undesirable for economic reasons. A wide variety of reactor types may be employed, including packed columns, stirred tanks, tubular reactors, etc. At higher temperatures, in the case of a gaseous alkene, the rate of reaction may become limited by mass transfer of the alkene from the gas phase to the liquid phase containing the catalyst, and reactors capable of faster mass transfer will enable faster reaction and shorter contact time. Less effective reactors will require longer reaction time. Effective reactors for gas-liquid reactions are well known to those skilled in the art, and are described, for example in Table 2-1 on page 41 of A. Gianetto et al., "Multiphase Chemical Reactors; Theory, Design, Scaleup," Hemisphere Publishing Corp. (1986). The metallacycle is then fed to another reactor and reacted with hydrogen, typically at temperatures from 0° to 200° C., at hydrogen pressures of 100 to 10,000 kPa (about 1 atm. to 100 atm.) and at a contact time of from about 1 minute to about 24 hours to form a $HC(R^1)_2C(R^1)_2C(R^2)_2C(R^2)_2H$ product compound. The hydrogen pressure employed depends to some extent on the particular metallacycle being hydrogenated and the desired rate and conversion. Theoretically at least one mole of $H_2$ per mole of metallacycle is required to achieve complete conversion of metallacycle to product compound, but higher or lower amounts may be employed if desired. As before, the temperature and pressure may be varied depending to a certain extent on the particular metallacycle being hydrogenated and the desired rate. Higher temperatures and pressures result in faster hydrogenation, which leads to a shorter required contact time to reach any given conversion. The product compound is recovered from the reactor by conventional separation techniques such as distillation. Fluorosubstituted hydrocarbons of the formula $HC(R^1)_2C(R^1)_2C(R^2)_2C(R^2)_2H$ may form azeotropes with HF, with olefinic starting materials, with solvents, and with minor hydrofluorocarbon products. Conventional decantation/distillation may be employed if further purification of the hydrofluorocarbons is desired. The $ML_m$ metal complex liberated during the hydrogenolysis of the $L_mM(1,4\text{-}C(R^1)_2C(R^1)_2C(R^2)_2C(R^2)_2\text{---})$ metallacycle may be recycled to the reactor in which the olefin addition is done. The $ML_m$ metal complex may be stabilized prior to reaction with the $C(R^1)_2\text{=}C(R^1)_2$ and $C(R^1)_2\text{=}C(R^2)_2$ olefins by addition of ligands as defined above to the solvent.

Examples of this embodiment of the invention, are represented by the reaction of an $NiL_4$ or an $NiL_3$ complex, where L is mono- or bidentate phosphine or phosphite ligand selected from the group consisting of $P(n\text{-}C_4H_9)_3$, $P(C_2H_5)_3$, $P(OCH(CH_3)_2)_3$, $P(O\text{-}ortho\text{-}tolyl)_3$, diphite, and monophite in a solvent selected from the group consisting of pentane, hexanes, cyclohexane, benzene, chlorobenzene, toluene, xylene, methyl acetate, methyl formate, and tetrahydrofuran, with an olefin such as tetrafluoroethene. The metallacycle formation reaction is typically done with a mole ratio of alkene to metal of from about 1:1 to about 20:1 at a temperature of from about 50° C. to 150° C. and pressures between about 100 kPa and 500 kPa (about 1 atm. and 5 atm.) with contact times of about 1 minute to 6 hours. The resulting product is a metallacycle of the formula $NiL_2(1,4\text{-}(CF_2)_4\text{---})$, dissolved in the solvent, where L2 represents two monodentate phosphine or phosphite ligands or one bidentate phosphine or phosphite ligand. An especially preferred nickel metallacycle for the preparation of 1,1,2,2,3,3,4,4-octafluorobutane is the complex $NiL_2(1,4\text{-}(CF_2)_4\text{---})$ where each L is $P(OCH(CH_3)_2)_3$.

The $NiL_2(1,4\text{-}(CF_2)_4\text{---})$ solution is then reacted with hydrogen, typically at a temperature of from about 80° C. to 180° C. and a hydrogen pressure between about 1000 and 7000 kPa (about 10 atm. and 70 atm.) with a contact time of from about 15 minutes to 8 hours. The hydrogenolysis product, 1,1,2,2,3,3,4,4-octafluorobutane (HFC-338pcc), is separated by conventional techniques such as distillation. The remaining $NiL_2$ fragment which may be stabilized by the presence of excess ligand L, is recycled to the metallacycle formation reactor where it is contacted with additional tetrafluoroethene under the same conditions as described above for the metallacycle formation step.

In a second embodiment of this invention a metal complex of the type $M_xL_n$ or a metallacycle of the type $L_mM(1,4\text{-}(CF_2)_4\text{---})$ dissolved in a suitable solvent as described above, is treated with an olefinic compound of the formula $(R^2)_2C\text{=}C(R^2)_2$, and another or the same olefinic compound of the formula $(R^1)_2C\text{=}C(R^1)_2$, where $R^1$ and $R^2$ are as defined above, and then reacted with hydrogen, typically at a temperature from 0° C. to 200° C., at a hydrogen pressure of from 100 to 10,000 kPa (about 1 atm. to 100 atm.) and at a contact time of 1 hour to 24 hours, such that the mole ratios of $(R^1)_2C\text{=}C(R^1)_2$ and $(R^2)_2C\text{=}C(R^2)_2$ to metal are from about 0.1:1 to 100:1, to form the $HC(R^1)_2C(R^1)_2C(R^2)_2C(R^2)_2H$ product compound directly. That is, the metallacycle is reacted with hydrogen to give the $HC(R^1)_2C(R^1)_2C(R^2)_2C(R^2)_2H$ product compound and a metal fragment, which can react with additional olefin to form additional metallacycle. In the case where $(R^1)_2C\text{=}C(R^1)_2$ and $(R^2)_2C\text{=}C(R^2)_2$ are different alkenes and/or where the alkenes are nonsymetric, it may be possible to form a number of different metallacycles, depending on whether the two alkenes incorporated in the metallacycle are different or the same and/or on the orientation of the two alkene reactants (i.e., head to head, tail to tail, or head to tail). The relative amounts of the two alkenes used can be varied over a wide range, and depend to some extent on the particular metal employed, the differential reactivity of the two alkenes toward that metal, and the particular metallacycle product desired. Normally the preferred ratio of $(R^1)_2C\text{=}C(R^1)_2$ to $(R^2)_2C\text{=}C(R^2)_2$ is from about 0.01:1 to 100:1. The $HC(R^1)_2C(R^1)_2C(R^2)_2C(R^2)_2H$ product compound (s) may be recovered from the reactor as discussed for the first embodiment.

Examples of this second embodiment of the invention, are represented by the reaction of an $NiL_4$ or an $NiL_3$ complex, where L is mono- or bidentate phosphine or phosphite ligand selected from the group consisting of $P(n\text{-}C_4H_9)_3$, $P(C_2H_5)_3$, $P(OCH(CH_3)_2)_3$, $P(O\text{-}ortho\text{-}tolyl)_3$, diphite, and monophite in a solvent selected from the group consisting of pentane, hexanes, cyclohexane, benzene, chlorobenzene, toluene, xylene, methyl acetate, methyl formate and tetrahydrofuran, with an olefin, such as tetrafluoroethene, and with hydrogen at a temperature of from about 80° C. to about 180° C., at a pressure of from about 1000 to 7000 kPa (about 10 atm. to about 70 atm.) and at a contact time of from about 0.5 hour to about 5 hours. The hydrogenolysis product, 1,1,2,2,3,3,4,4-octafluorobutane (HFC-338pcc), is separated by conventional techniques such as distillation.

In a third embodiment of this invention, the metal complex, $M_xL_n$, is dissolved in an appropriate solvent, and reacted with an olefinic compound of the type $(R^2)_2C\text{=}C(R^2)_2$, where $R^2$ is as defined above, at temperatures from −25° C. to 200° C., at pressures of from 5 kPa to 10,000 kPa (0.05 atm. to 100 atm.) and at a contact time of 1 minute to 24 hours to form an olefin complex of the type $L_mM(\eta^2\text{-}C(R^2)_2C(R^2)_2)$. Olefin complexes of this type are known (see, e.g., Tolman et al., J. American Chemical Society, Vol. 96, p. 2774 (1974)). Normally for this embodiment two or more $R^2$ groups are other than F. The mole ratio of olefinic compound to metal employed may vary over a wide range, from about 0.1:1 about 100:1. The preferred ratio is from about 0.5:1 to 10:1 and depends to some extent on the particular metal complex and olefinic compound employed, and the desired rate and conversion of $M_xL_n$ to olefin complex. Theoretically, a mole ratio of 1 olefin per metal is required to achieve complete conversion of $M_xL_n$ to olefin complex. It may be desirable to use mole ratios greater than 1 to decrease the time required for olefin complex formation or to ensure complete conversion of the limiting reagent, $M_xL_n$, to olefin complex. The excess olefin or its hydrogenation product may then be recovered for recycle or disposal. To avoid this recovery step, it may be desirable to reduce the amount of olefin employed to less than 1 per metal, so that the olefin is the limiting reagent and is completely consumed. This results in less than complete conversion of $M_xL_n$ to olefin complex, but avoids the presence of excess olefin in the olefin complex product. The olefin complex $L_mM(\eta^2\text{-}C(R^2)_2C(R^2)_2)$ can then be reacted (even without purification or isolation of the olefinic complex) with the other olefinic compound of the type $(R^1)_2C=C(R^1)_2$, where $R^1$ is as defined above, in the same or a different reactor to form the metallacycle. Typically, this reaction is accomplished at temperatures from $-25°$ C. to $200°$ C., at pressures of 5 to 10,000 kPa (about 0.05 atm. to 100 atm.) and at a contact time of 1 minute to 24 hours to form a metallacycle $L_mM(1,4\text{-}C(R^1)_2C(R^1)_2C(R^2)_2C(R^2)_2\text{—})$. The mole ratio of olefin to olefin complex employed may vary over a wide range and is typically from about 0.1:1 to about 100:1. The preferred ratio is from about 1:1 to 10:1 and depends to some extent on the particular olefin complex and olefin employed, and the desired rate and conversion of olefin complex to metallacycle. Theoretically, a mole ratio of 1 olefin per metal is required to achieve complete conversion of olefin complex to metallacycle. It may be desirable to use mole ratios greater than 1 to decrease the time required for metallacycle formation or to ensure complete conversion of the limiting reagent, olefin complex, to metallacycle. The excess olefin or its hydrogenation product may then be recovered for recycle or disposal. To avoid this recovery step, it may be desirable to reduce the amount of olefin employed to less than 1 per metal, so that the olefin is the limiting reagent and is completely consumed. This results in less than complete conversion of olefin complex to metallacycle, but avoids the presence of excess olefin in the metallacycle product. The metallacycle $L_mM(1,4\text{-}C(R^1)_2C(R^1)_2C(R^2)_2C(R^2)_2\text{—})$ is then treated with hydrogen in the same or a different reactor at temperatures from $0°$ C. to $200°$ C., at pressures of about 100 to 10,000 kPa (about 1 atm. to 100 atm.) and at a contact time of 1 minute to 24 hours. This embodiment is particularly advantageous when the olefinic compounds $C(R^1)_2=C(R^1)_2$ and $C(R^2)_2=C(R^2)_2$ are different and it is desired to minimize the amounts of metallacycle $L_mM(1,4\text{-}C(R^1)_2C(R^1)_2C(R^1)_2C(R^1)_2\text{—})$ and $L_mM(1,4\text{-}C(R^2)_2C(R^2)_2C(R^2)_2C(R^2)_2\text{—})$ that may be formed when both olefinic compounds are fed to the $M_xL_n$ metal complex at the same time. Product separation and catalyst recycle are carried out in the manner described above.

A preferred example of this third embodiment of the invention, is the formation of a nickel olefin complex of type $L_2Ni(\eta^2\text{-}C(R^2)_2C(R^2)_2)$ by reaction of an $NiL_4$ or an $NiL_3$ complex, where L is mono- or bidentate phosphine or phosphite ligand selected from the group consisting of $P(n\text{-}C_4H_9)_3$, $P(OC_2H_5)_3$, $P(OCH(CH_3)_2)_3$, $P(O\text{-orthotolyl})_3$, diphite, and monophite in a solvent selected from the group consisting of pentane, hexanes, cyclohexane, benzene, chlorobenzene, toluene, xylene, methyl acetate, methyl formate, and tetrahydrofuran, with an olefin, $C(R^2)_2=C(R^2)_2$, where $R^2$ is selected from the group H, Cl, and F (for example, ethylene, vinyl chloride, vinyl fluoride, acrylonitrile, methyl acrylate, vinylidene fluoride). The nickel-olefin complex $L_2Ni(\eta^2\text{-}C(R^2)_2C(R^2)_2)$ is then reacted with a second olefinic compound, $C(R^1)_2=C(R^1)_2$.

Preferably each $R^1$ is selected from the group H, Cl, and F, and at least two of $R^1$ groups (and more preferably at least 3 $R^1$ groups) are F. Examples of such olefins include those selected from the group consisting of tetrafluoroethene, chlorotrifluoroethene, trifluoroethene, $CH_2=CF_2$ and perfluoromethylvinylether. The reaction is carried out in the same or in a different reactor, at temperatures from $0°$ C. to $200°$ C., at pressures of about 100 to 10,000 kPa (about 1 atm. to about 100 atm.) and at a contact time of from 1 minute to 24 hours to form a metallacycle $L_2Ni(1,4\text{-}C(R^1)_2C(R^1)_2C(R^2)_2C(R^2)_2\text{—})$ where $R^1$ and $R^2$ are as defined above. The metallacycle $L_2Ni(1,4\text{-}C(R^1)_2C(R^1)_2C(R^2)_2C(R^2)_2\text{—})$ is then treated with hydrogen in the same or a different reactor at temperatures from $0°$ C. to $200°$ C., at pressures of 1 atm. to 100 atm. and at a contact time of 1 minute to 24 hours to form the product compound $HC(R^1)_2C(R^1)_2C(R^2)_2C(R^2)_2H$. In the case where $C(R^2)_2=C(R^2)_2$ is ethene (i.e., each $R^2$ is H) and $C(R^1)_2=C(R^1)_2$ is tetrafluoroethene (i.e., each $R^1$ is F), the product compound is 1,1,2,2-tetrafluorobutane (HFC-374pc).

In a fourth embodiment of this invention, a mixture of the metallacyclic compound, $L_mM(1,4\text{-}C(R^1)_2C(R^1)_2C(R^2)_2C(R^2)_2\text{—})$ and at least one reactant selected from the group consisting of olefinic complexes of the type $L_mM(\eta^2\text{-}C(R^1)_2C(R^1)_2)$ and $L_mM(\eta^2\text{-}C(R^2)_2C(R^2)_2)$, and olefinic compounds of the formulas $C(R^2)_2=C(R^2)_2$ and $C(R^1)_2=C(R^1)_2$, may be reacted with hydrogen to produce a product mixture containing in addition to the product compound, $HC(R^1)_2C(R^1)_2C(R^2)_2C(R^2)_2H$ H, at least one compound selected from the group consisting of $HC(R^2)_2C(R^2)H$ and $HC(R^1)_2C(R^1)_2H$. This is illustrated in Examples 2, 21 and 22 below for the metallacycles $(OC)_4Fe(1,4\text{-}CF_2CF_2CF_2CF_2\text{—})$ and $NiL_2(1,4\text{-}CF_2CF_2CF_2CF_2\text{—})$ where L is $P(OCH(CH_3)_2)_3$, respectively.

The preferred embodiment depends to some extent on the particular metal complex employed and on the relative reactivity of the two alkenes employed. In cases where one alkene is capable of forming a metallacycle on its own, but the other is not (i.e., is less reactive), formation of a mixed metallacycle can be favored by adding more of the less reactive olefin, or by use of embodiment 3, wherein the less reactive olefin can be added first. In cases where both olefins are capable of forming metallacycles on their own, use of embodiment 1 or 2 may be preferable, where the two olefins may be reacted at the same time, with their relative amounts being adjusted to favor formation of the desired metallacycle. In cases where one olefin is capable of forming a stable olefin complex, embodiment 3 may be particularly useful for preparation of mixed metallacycles. Generally speaking, olefins having more fluorine substituents (e.g., three or four) are more reactive than olefins having fewer fluorine substituents (e.g., zero or one).

For metallacycles of the class, $L_4M(1,4\text{-}CFR^1CFR^1C(R^2)_2C(R^2)_2\text{—})$ where M is Fe or Ru and L is CO, phosphine, phosphite, or N-donor ligand, the reaction with hydrogen may be used to produce one or more additional compounds where one or more fluorine substituents on the carbon atoms bound to the metal are also replaced by hydrogen. This additional hydrogen addition results in HF production. For example, in the case where M is Fe, L is CO, and each $R^1$ and $R^2$ is F, hydrogenolysis of the metallacycle can produce $HCF_2CF_2CF_2CF_2H$ as well as at least one additional compound selected from $HCF_2CF_2CF_2CFH_2$ and $C_4H_4F_6$ isomers as illustrated in Example 1. Homogeneous or heterogeneous catalysts selected from Periodic Table Groups 8, 9, or 10 as defined above may be advantageously employed. Such catalysts include metal complexes such as RuHCl (PPh$_3$)$_3$, RhCl(PPh$_3$)$_3$, and (Rh(COD)(DPPB))BF$_4$ and supported metal catalysts such as Pd on carbon or Rh on carbon.

A noteworthy embodiment of this invention involves the manufacture of HCF$_2$CF$_2$CF$_2$CF$_2$H by (a) reacting in the liquid phase F$_2$C=CF$_2$ and a metal complex soluble in the liquid phase of the formula M$_x$L$_n$ to form a metallacycle of the formula

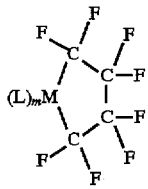

wherein M is a metal selected from the group consisting of Group 8 metals, Group 9 metals, and Group 10 metals, L is a ligand selected from the group consisting of Group 14 ligands, Group 15 ligands, and Group 16 ligands, x is an integer from 1 to 3, n is an integer from 1 to 12 and m is an integer from 1 to 4; and (b) reacting said cyclic compound with hydrogen. Preferably, L is triisopropyl phosphite, M is Ni, x is 1, n is 4, and m is 2. The F$_2$C=CF$_2$ and the metal complex may advantageously be reacted, for example, in a solvent selected from the group consisting of pentane, hexanes, cyclohexane, benzene, chlorobenzene, toluene, xylene, methyl acetate, methyl formate and tetrahydrofuran. Also of note are embodiments wherein the F$_2$C=CF$_2$ and the metallic ligand compound are reacted in HCF$_2$CF$_2$CF$_2$CF$_2$H.

The process of this invention enables production of various compounds of the formula HC(R$^1$)$_2$C(R$^1$)$_2$C(R$^2$)$_2$C(R$^2$)$_2$H. Of note are product compositions comprising compounds of the formula HCFR$^1$CFR$^1$CHR$^2$CH$_2$R$^2$ where each R$^1$ is selected from the group consisting of H, Cl, F, CN, and OCF$_3$ (provided that at least one R$^1$ is F) and R$^2$ is as defined above. Included are such product compositions comprising compounds where each R$^2$ is selected from the group consisting of H, Cl, F, CN, OCF$_3$, CO$_2$CH$_3$, C$_6$H$_5$, and CF$_3$, provided that at least one R$^2$ is H, and such product compositions comprising compounds where the two R$^2$ groups together form a link selected from the group consisting of —CH$_2$CH$_2$CH$_2$—, —CH$_2$CH$_2$CH$_2$CH$_2$—, —CH$_2$CH$_2$CH(CH$_3$)—, —CH$_2$CH(CH$_3$)CH$_2$—, —C(O)OC(O)—, and norborndiyl (i.e., where the —CHR$^2$CHR$^2$— fragment is derived from cyclopentene, 3-methylcyclopentane, 4-methylcyclopentene, cyclohexene, maleic anhydride, or norborene). For example, the process of this invention enables production of CHF$_2$CF$_2$CH$_2$CH$_3$ (derived from CF$_2$=CF$_2$ and CH$_2$=CH$_2$); CHF$_2$CH$_2$CH$_2$CHF$_2$ (derived from CF$_2$=CH$_2$); CHClCF$_2$CClFCHF$_2$ and CHClFCF$_2$CF$_2$CHClF (derived from CClF=CF$_2$); CF$_3$OCHFCF$_2$CF$_2$CHFOCF$_3$, CHF$_2$CF(OCF$_3$)CF$_2$CHFOCF$_3$, and CHF$_2$CF(OCF$_3$)CF(OCF$_3$)CHF$_2$ (derived from CF$_3$OCF=CF$_2$); CH(CN)FCF$_2$CF$_2$CHF(CN), CHF$_2$CF(CN)CF$_2$CHF(CN), and CHF$_2$CF(CN)CF(CN)CHF$_2$ (derived from CF(CN)=CF$_2$); CH$_2$FCH$_2$CF$_2$CHF$_2$ and CH$_3$CHFCF$_2$CHF$_2$ (derived from CH$_2$=CHF and CF$_2$=CF$_2$); CH$_3$CHFCHFCHF$_2$, CH$_2$FCH$_2$CHFCHF$_2$, CH$_2$FCH$_2$CF$_2$CH$_2$F, and CH$_3$CHFCF$_2$CH$_2$F (derived from CH$_2$=CHF and CHF=CF$_2$); CH$_3$CH$_2$CClFCHF$_2$ and CH$_3$CH$_2$CF$_2$CHClF (derived from CH$_2$=CH$_2$ and CClF=CF$_2$); CH$_2$FCH$_2$CClFCHF$_2$, CH$_3$CHFCClFCHF$_2$, and CH$_2$FCH$_2$CF$_2$CHClF (derived from CH$_2$=CHF and CClF=CF$_2$); CH$_3$CH$_2$CF(OCF$_3$)CHF$_2$ and CH$_3$CH$_2$CF$_2$CHFOCF$_3$ (derived from CH$_2$=CH$_2$ and CF$_2$=CFOCF$_3$); CH$_2$FCH$_2$CF(OCF$_3$)CHF$_2$, CH$_3$CHFCF(OCF$_3$)CHF$_2$, CH$_2$FCH$_2$CF$_2$CHFOCF$_3$, and CH$_3$CHFCF$_2$CHFOCF$_3$ (derived from CH$_2$=CHF and CF$_2$=CFOCF$_3$); CH$_2$ClCH$_2$CClFCHF$_2$, CH$_3$CHClCClFCHF$_2$, and CH$_2$ClCH$_2$CF$_2$CHClF (derived from CH$_2$=CHCl and CClF=CF$_2$); CH$_2$ClCH$_2$CF$_2$CHF$_2$ and CH$_3$CHClCF$_2$CHF$_2$ (derived from CH$_2$=CHCl and CF$_2$=CF$_2$); CH$_3$CHClCHFCHF$_2$, CH$_2$ClCH$_2$CHFCHF$_2$, CH$_2$ClCH$_2$CF$_2$CH$_2$F, and CH$_3$CHClCF$_2$CH$_2$F (derived from CH$_2$=CHCl and CHF=CF$_2$); CH$_2$ClCH$_2$CF(OCF$_3$)CHF$_2$, CH$_3$CHClCF(OCF$_3$)CHF$_2$, CH$_2$ClCH$_2$CF$_2$CHFOCF$_3$, and CH$_3$CHClCF$_2$CHFOCF$_3$ (derived from CH$_2$=CHCl and CF$_2$=CFOCF$_3$); CH$_3$CH(CN)CF$_2$CHF$_2$ and CH$_2$CNCH$_2$CF$_2$CHF$_2$ (derived from CH$_2$=CHCN and CF$_2$=CF$_2$); CH$_3$CH(CO$_2$CH$_3$)CF$_2$CHF$_2$ and CH$_3$OC(O)CH$_2$CH$_2$CF$_2$CHF$_2$ (derived from CH$_2$=CHCO$_2$CH$_3$ and CF$_2$=CF$_2$); C$_6$H$_5$CH$_2$CH$_2$CF$_2$CHF$_2$ and CH$_3$CH(C$_6$H$_5$)CF$_2$CHF$_2$ (derived from CH$_2$=CHC$_6$H$_5$ and CF$_2$=CF$_2$); CF$_3$CH$_2$CH$_2$CF$_2$CHF$_2$ and CH$_3$CH(CF$_3$)CF$_2$CHF$_2$ (derived from CH$_2$=CHCF$_3$ and CF$_2$=CF$_2$); CH$_2$CNCH(CN)CF$_2$CHF$_2$ (derived from cis- or trans-CHCN=CHCN and CF$_2$=CF$_2$); and

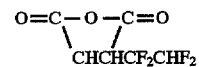

(derived from maleic anhydride and CF$_2$=CF$_2$).

Other compounds which may be made by the process of this invention include CHF$_2$CF$_2$CF$_2$CHF$_2$ (derived from CF$_2$=CF$_2$); CHF$_2$CClFCClFCHF$_2$ (derived from CClF=CF$_2$); CH$_2$FCF$_2$CHFCHF$_2$, CH$_2$FCF$_2$CF$_2$CH$_2$F, and CHF$_2$CHFCHFCHF$_2$ (derived from CHF=CF$_2$); CHF$_2$CH$_2$CF$_2$CH$_3$ and CH$_3$CF$_2$CF$_2$CH$_3$ (derived from CH$_2$=CF$_2$); CH$_3$CF$_2$CF$_2$CHF$_2$ and CHF$_2$CH$_2$CF$_2$CHF$_2$ (derived from CF$_2$=CH$_2$ and CF$_2$=CF$_2$); CH$_3$CHFCF$_2$CHClF (derived from CH$_2$=CHF and CClF=CF$_2$); and CH$_3$CHClCF$_2$CHClF (derived from CH$_2$=CHCl and CClF=CF$_2$). Compositions provided by this invention include certain product compounds themselves, and compositions which include certain product compounds in combination with other components. For example, the product compounds from the hydrogenolysis of this invention are miscible with various solvents conventionally used in cleaning operations. Compositions suitable for use in cleaning operations can be prepared which comprise a mixture of the product compound(s) with one or more compounds selected from the group consisting of alcohols, ethers, esters, ketones, nitromethane, acetonitrile, and halogenated hydrocarbons. The preferred alcohols and halogenated hydrocarbons contain from 1 to 4 carbon atoms; the preferred ethers contain from 2 to 6 carbon atoms; and the preferred esters and ketones contain from 3 to 6 carbon atoms. Examples of suitable alcohols include methanol, ethanol, and isopropanol. Examples of suitable ethers include tetrahydrofuran, methyl t-butylether and diethylether. Examples of suitable ketones include acetone and methyl ethyl ketone. Examples of suitable halogenated hydrocarbons include methylene chloride (i.e., dichloromethane), 1,1,2-trichloro-1,2,2-trifluoroethane, dichlorodifluoroethane, trichloroethene, and trans-1,2-dichloroethylene. Preferably, such compositions contain at least about 5 percent by weight total of the product compound(s); and can contain up to 99 percent by weight, or even more thereof. Preferred compositions include mixtures of HCF$_2$CF$_2$CF$_2$CF$_2$H, CH$_3$CH$_2$CF$_2$CF$_2$H, and $CH_2FCF_2CF_2CF_2H$ (especially $HCF_2CF_2CF_2CF_2H$) with one or more of said alcohols, ethers, esters, ketones, nitromethane, acetonitrile and halogenated hydrocarbons. Most preferred with respect to ozone depletion potential are compositions in which no component contains chlorine.

The mixtures of this invention are useful in a wide variety of processes for cleaning solid surfaces which comprise treating said surface therewith. Applications include removal of flux and flux residues from printed circuit boards contaminated therewith.

Compositions which comprise an admixture of effective amounts of one or more of the product compounds with one or more solvents selected from the group consisting of alcohols, ethers, esters, ketones, nitromethane, acetonitrile, and halogenated hydrocarbons to form an azeotrope or azeotrope-like mixture are considered especially useful. Reference is made to U.S. Pat. Nos. 5,250,208, 5,221,493 and 5,194,170 for providing examples of certain azeotrope admixtures.

The compositions may be used in conventional apparatus, employing conventional operating techniques. The solvent(s) may be used without heat if desired, but the cleaning action of the solvent may be assisted by conventional means (e.g., heating, agitation, etc.). In some applications (e.g., removing certain tenacious fluxes from soldered components) it may be advantageous to use ultrasonic irradiation in combination with the solvent(s).

Compositions provided in accordance with this invention can be used in cleaning processes such as are described in U.S. Pat. Nos. 3,881,949 and 4,715,900.

The mixtures can be prepared by any convenient method including mixing or combining the desired amounts of the components. A preferred method is to weigh the desired amounts of each component and thereafter combine them in an appropriate container.

Of note are mixtures which comprise one or more of the product compounds in combination with a solvent which is used for the process for its production and can also be used in combination with the product compound as a cleaning mixture. Examples include mixtures of product compound (s) with a solvent selected from the group consisting of aliphatic hydrocarbons such as pentane, 2-methyl pentane, 3-methyl pentane, 2,2-dimethyl butane, 2,3-dimethyl butane, hexane, and heptane; cyclic aliphatic hydrocarbons such as cyclopentane, methyl cyclopentane, cyclohexane, and methyl cyclohexane; aromatic hydrocarbons such as fluorobenzene and toluene; aliphatic esters such as methyl formate, ethyl formate, n-propyl formate, tert-butyl formate, methyl acetate, ethyl acetate, and isopropyl acetate; cyclic and acyclic aliphatic ethers such as methyl tert-butyl ether, 1,2-dimethoxyethane, and tetrahydrofuran; fluorinated aliphatic ethers such as 1,1,2,2-tetrafluoroethyl methyl ether, and 1,1,2,2-tetrafluoroethyl ethyl ether; ketones such as acetone, methyl ethyl ketone; aliphatic nitriles such as acetonitrile and propionitrile; and nitromethane or mixtures thereof. Azeotropic combinations are considered particularly useful.

Also of note are mixtures of two or more product compounds (e.g., a mixture of $CHF_2CF_2CF_2CHF_2$ and $CH_3CH_2CF_2CF_2H$ or a mixture of $CHF_2CF_2CF_2CHF_2$ and $CH_2FCF_2CF_2CF_2H$) which can themselves be used for cleaning compositions, either alone or in further combination with other solvents.

Product compounds such as $HCF_2CF_2CF_2CF_2H$ are also considered useful either alone or in combination with other conventional ingredients (e.g., hydrofluorocarbons, stabilizers, etc.) as agents for fire extinguishants, refrigerants, heat transfer media, foam expansion compositions, aerosol propellants, power cycle working fluids, and sterilant gas carriers.

Compounds of this invention include those of the formula $L_2Ni(1,4-CR^1_2CR^1_2CR^2_2CR^2_2—)$ where $R^1$, $R^2$ and L are defined as indicated above, provided that when each L is a Group 15 ligand as defined above, and each $R^1$ and $R^2$ is F, then L is not trimethylphosphite, tri-o-tolylphosphite, triethylphosphine, tributylphosphine, methyldiphenyl phosphine, triphenylphosphine, dimethylphenyl arsine, 4-methylpyridine, dimethylarsine, 2,2-bipyridyl, or 1,2-bis (diphenyl phosphino)ethane, and provided that when three $R^1$ groups and three $R^2$ groups are F and the remaining $R^1$ group and $R^2$ group are H, then L is not triphenylphosphine or methydiphenylphosphine. Of note are compounds where at least three $R^1$ groups are F and at least one $R^2$ group is not F. Preferred compounds of this type include those of the formula

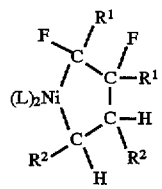

where each $R^1$ is selected from the group consisting of H, Cl, F, $OCF_3$, and CN, provided that at least one $R^1$ is F, and each $R^2$ is selected as indicated above. Preferred compounds of this type also include compounds where each $R^2$ is selected from the group consisting of H, Cl, F, CN, $CF_3$, $C_6H_5$, and $CO_2CH_3$, provided that at least one $R^2$ is H; and compounds where each $R^1$ and $R^2$ is F (subject to the indicated proviso).

Examples include $L_2Ni(1,4-CF_2CF_2CH_2CH_2—)$ (which may be derived from $CH_2=CH_2$ and $CF_2=CF_2$); $L_2Ni(1, 4-CF_2CH_2CH_2CF_2—)$, $L_2Ni(1,4-CH_2CF_2CF_2CH_2—)$, and $L_2Ni(1,4-CF_2CH_2CF_2CH_2—)$ (which may be derived from $CF_2=CH_2$); $L_2Ni(1,4-CClFCF_2CClFCF_2—)$, $L_2Ni(1,4-CClFCF_2CF_2CClF—)$, and $L_2Ni(1,4-CF_2CClFCClFCF_2—)$ (which may be derived from $CClF=CF_2$); $L_2Ni(1,4-(CF_3O)CFCF_2CF_2CF(OCF_3)—)$, $L_2Ni(1,4-CF_2CF(OCF_3)CF_2CF(OCF_3)—)$, and $L_2Ni(1,4-CF_2CF(OCF_3)CF(OCF_3)CF_2—)$ (which may be derived from $CF_3OCF=CF_2$); $L_2Ni(1,4-C(CN)FCF_2CF_2CF(CN)—)$, $L_2Ni(1,4-CF_2CF(CN)CF_2CF(CN)—)$, and $L_2Ni(1,4-CF_2CF(CN)CF(CN)CF_2—)$ (which may be derived from $CF(CN)=CF_2$); $L_2Ni(1,4-CHFCH_2CF_2CF_2—)$ and $L_2Ni(1,4-CH_2CHFCF_2CF_2—)$ (which may be derived from $CH_2=CHF$ and $CF_2=CF_2$); $L_2Ni(1,4-CH_2CHFCHFCF_2—)$, $L_2Ni(1,4-CHFCH_2CHFCF_2—)$, $L_2Ni(1,4-CHFCH_2CF_2CHF—)$, and $L_2Ni(1,4-CH_2CHFCF_2CHF—)$ (which may be derived from $CH_2=CHF$ and $CHF=CF_2$); $L_2Ni(1,4-CH_2CH_2CClFCF_2—)$ and $L_2Ni(1,4-CH_2CH_2CF_2CClF—)$ (which may be derived from $CH_2=CH_2$ and $CClF=CF_2$); $L_2Ni(1,4-CHFCH_2CClFCF_2—)$, $L_2Ni(1,4-CH_2CHFCClFCF_2—)$, $L_2Ni(1,4-CHFCH_2CF_2CClF—)$, and $L_2Ni(1,4-CH_2CHFCF_2CClF—)$ (which may be derived from $CH_2=CHF$ and $CClF=CF_2$); $L_2Ni(1,4-CH_2CH_2CF(OCF_3)CF_2—)$ and $L_2Ni(1,4-CH_2CH_2CF_2CF(OCF_3)—)$ (which may be derived from $CH_2=CH_2$ and $CF_2=CFOCF_3$); $L_2Ni(1,4-CHFCH_2CF(OCF_3)CF_2—)$, $L_2Ni(1,4-CH_2CHFCF(OCF_3)CF_2—)$, $L_2Ni(1,4-CHFCH_2CF_2CF(OCF_3)—)$, and $L_2Ni(1,4-CH_2CHFCF_2CF(OCF_3)—)$ (which may be derived from $CH_2=CHF$ and $CF_2=CFOCF_3$); $L_2Ni(1,4-CHClCH_2CClFCF_2—)$, $L_2Ni(1,4-CH_2CHClCClFCF_2—)$, $L_2Ni(1,4-CHClCH_2CF_2CClF—)$, and $L_2Ni(1,4-CH_2CHClCF_2CClF—)$ (which may be derived from $CH_2=CHCl$ and $CClF=CF_2$); $L_2Ni(1,4-CHClCH_2CF_2CF_2—)$ and $L_2Ni(1,4-CH_2CHClCF_2CF_2—)$ (which may be derived from $CH_2=CHCl$ and $CF_2=CF_2$); $L_2Ni(1,4-CH_2CHClCHFCF_2—)$, $L_2Ni(1,4-CHClCH_2CHFCF_2—)$, $L_2Ni(1,4-CHClCH_2CF_2CHF—)$, and $L_2Ni(1,4-CH_2CHClCF_2CHF—)$ (which may be derived from $CH_2=CHCl$ and $CHF=CF_2$); $L_2Ni(1,4-CHClCH_2CF(OCF_3)CF_2—)$, $L_2Ni(1,4-CH_2CHClCF(OCF_3)CF_2—)$, $L_2Ni(1,4-CHClCH_2CF_2CHF(OCF_3)—)$, and $L_2Ni(1,4-CH_2CHClCF_2CF(OCF_3)—)$ (which may be derived from $CH_2=CHCl$ and $CF_2=CFOCF_3$); $L_2Ni(1,4-CH_2CH(CN)CF_2CF_2—)$ and $L_2Ni(1,4-CH(CN)CH_2CF_2CF_2—)$ (which may be derived from $CH_2=CHCN$ and $CF_2=CF_2$); $L_2Ni(1,4-CH_2CH(CO_2CH_3)CF_2CF_2—)$ and $L_2Ni(1,4-CH(CO_2CH_3)CH_2CF_2CF_2—)$ (which may be derived from $CH_2=CHCO_2CH_3$ and $CF_2=CF_2$); $L_2Ni(1,4-(C_6H_5)CHCH_2CF_2CF_2—)$ and $L_2Ni(1,4-CH_2CH(C_6H_5)CF_2CF_2—)$ (which may be derived from $CH_2=CHC_6H_5$ and $CF_2=CF_2$); $L_2Ni(1,4-(CF_3)CHCH_2CF_2CF_2—)$ and $L_2Ni(1,4-CH_2CH(CF_3)CF_2CF_2—)$ (which may be derived from $CH_2=CHCF_3$ and $CF_2=CF_2$).

Additional preferred compounds include those of the formula indicated above where each $R^1$ is selected from the group consisting of H, Cl, F, $OCF_3$, and CN, provided that at least one $R^1$ is F, and where both $R^2$s are CN, or where both $R^2$s together may comprise a link selected from the group $—CH_2CH_2CH_2—$, $—CH_2CH_2CH_2CH_2—$, $—CH_2CH_2CH(CH_3)—$, $—CH_2CH(CH_3)CH_2—$, C(O)OC(O), and

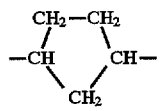

(that is, where the $C(R^2)HC(R^2)H$ fragment is derived from the olefinic compounds, cyclopentene, 3-methyl cyclopentene, 4-methyl cyclopentene, cyclohexene, maleic anhydride, or norbornene ).

Examples include $L_2Ni(1,4-CH(CN)CH(CN)CF_2CF_2—)$ (which may be derived from cis- or trans-$CHCN=CHCN$ and $CF_2=CF_2$);

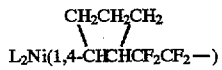

(which may be derived from cyclopentene and $CF_2=CF_2$);

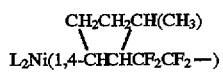

(which may be derived from 3-methyl cyclopentene and $CF_2=CF_2$);

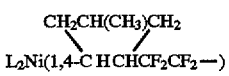

(which may be derived from 4-methyl cyclopentene and $CF_2=CF_2$);

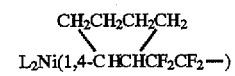

(which may be derived from cyclohexene and $CF_2=CF_2$);

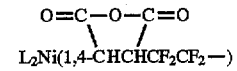

(which may be derived from maleic anhydride and $CF_2=CF_2$); and

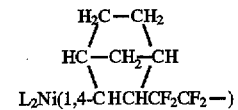

(which may be derived from norbornene and $CF_2=CF_2$). Also of note are compounds where each $R^1$ is F and each $R^2$ is H. Preferably L is a phosphine, a phosphinite, a phosphonite, or a phosphite ligand or a corresponding group 15 ligand where P is replaced by N, As, Sb or Bi.

Examples of said compounds include compounds of said formula wherein each $R^1$ is F, each $R^2$ is H, and L is tri-n-butyl phosphine, tri-p-tolylphosphite, tri-o-tolylphosphite, triethylphosphine, tri-isopropylphosphite, monophite, or diphite, and compounds where each $R^1$ and $R^2$ is F, and L is tri-p-tolylphosphite, triethylphosphine, tri-isopropylphosphite, triisooctylphosphite, monophite, or diphite.

Practice of the invention will become further apparent from the following non-limiting examples.

EXAMPLES

| | Ligand Abbreviations |
|---|---|
| DPPB | 1,4-bis(diphenylphosphine)butane |
| o-TTP | tri-o-tolyl phosphite |
| p-TTP | tri p-tolyl phosphite |
| TIPP | tri-isopropyl phosphite |
| COD | 1,5-cyclooctadiene |
| P(n-Bu)$_3$ | tri-n-butylphosphine |
| Nuclear Magnetic Resonance (NMR) Data Abbreviations | |
| q | quartet |
| s | singlet |
| d | doublet |
| t | triplet |
| br | broad peak |

General Conditions for Examples 1–3

Toluene and petroleum ether were distilled from sodium benzophenone ketyl. Benzene and methanol were dried with molecular sieves before use. The complex $Fe(CO)_4(1,4-(CF_2)_4—)$ was prepared from $Fe_2(CO)_9$ in toluene under 50 psi (446 kPa) of tetrafluoroethene at 80° C. for 16 hr using a Fischer-Porter tube. The nickel complexes $NiL_2(1,4-(CF_2)_4—)$ (L is $PEt_3$, P(O-p-tolyl)$_3$,) were prepared similarly from $NiL_4$, which was prepared from commercial $Ni(COD)_2$ and excess L. The metal complexes $RhCl(PPh_3)_3$, $RuHCl(PPh_3)_3$, and $(Rh(COD)(DPPB))BF_4$ were prepared by conventional methods and all other chemicals were obtained from commercial sources. Hydrogenolysis reactions in Examples 1–3 were performed in 10 mL shaker tubes which were loaded in an inert atmosphere glove box with constant nitrogen flush. Gases were charged and tubes were heated in a barricade and, upon completion, a vapor sample was taken for GC-MS (gas chromatography-mass spectrometry) analysis. The tube was then returned to the glove box, vented, and liquid samples obtained for NMR and IR spectroscopic analysis.

General Conditions for Examples 4–23

Reactions involving TFE or hydrogen in Examples 4–22 were performed in a 50 cc nickel alloy autoclave from Autoclave Engineers, Erie, Pa., agitated with a Rushton-type gas-inducing turbine blade impeller. Reactions involving hydrogen and TFE together were done in 75 cc shaker tubes inside a barricaded area due to the potential explosion hazards of such mixtures.

Analytical Procedures

GC-MS runs were run using a 20' (6.1 m)×⅛" (0.32 mm) Krytox™ (polyfluoroether) 143 HMW on 60/80 mesh (about 0.25/0.18 mm) Carbopack™ B (graphitized carbon) column. IR spectra were recorded on Perkin-Elmer 983G and Nicolet 205 FTIR spectrometers and NMR spectra were run on Nicolet 200 (188 MHz $^{19}$F) and GE 300 (300 MHz $^{1}$H, 121 MHz $^{31}$P, 282 MHz $^{19}$F) spectrometers. Positive F and P shifts are reported as ppm downfield of $CFCl_3$ (Freon 11) or external $H_3PO_4$ respectively.

Example 1

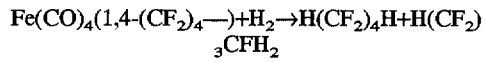

In a typical reaction, 100 mg $Fe(CO)_4(1,4-(CF_2)_4—)$ and the appropriate amount of catalyst were dissolved (or suspended) in toluene in a 10 mL shaker tube in the glove box. The sample was removed from the glove box and placed in a barricaded facility, pressurized with $H_2$ and heated at 100° C. for 20 hours. A gas sample was taken and the shaker tube was returned to the glove box. The tube was carefully vented and a portion of the reaction contents was dissolved in 1 mL of cold toluene for $^{19}$F NMR analysis. All runs were done at 500 psig (3550 kPa) hydrogen pressure except for run 11 which was done at 500 psig (3550 kPa) $H_2$ (1)/CO (1) pressure. The hydrogenolysis time was 20 hours for all runs except for runs 5 and 6 which were reacted with hydrogen for 10 hours. The reaction temperature was 100° C. in all cases. Reaction results are shown in Table 1. Injection of gaseous $Fe(CO)_4(1,4-(CF_2)_4—)$ into the GC-MS gave perfluorocyclobutene.

Perfluorocyclobutane was found in the amounts shown in the vapor phase of the following runs: 3 (1%); 11 (3%); and 12 (1%). An unknown compound was found in the amounts shown in the vapor phase of the following runs: 4 (6%); 6 (23%); 8 (2.5%); 10 (1%); and 12 (3%).

Example 2

To a solution of 200 mg (0.4 mmol) $Fe_3(CO)_{12}$ in 5 mL of toluene in a shaker tube was added 1 g (0.8 mmol) tetrafluoroethylene and 500 psig (3550 kPa) $H_2$. The reaction was heated at 100° C. for 20 hours and a gas sample taken. GC-MS analysis showed $CHF_2CHF_2$, $CH_2=CF_2$, $CF_2HCFH_2$, $CH_2F_2$, perfluorocyclobutane, and $H(CF_2)_4H$ in a 110:15:5:1:1:1 ratio.

Example 3

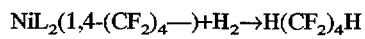

$Ni(P (Et)_3)_2(1,4-(CF_2)_4—)$ was prepared as described in C. S. Cundy et al., *J. Chem. Soc.* (A), 1970, 1647–53. $Ni(P(O-p-tol)_3)_2(1,4-(CF_2)_4—)$ was prepared as described in C. A. Tolman et al., *J. Am. Chem. Soc.*, 1974, 96, 2774–80.

Three reactions were conducted in a similar manner as for the iron analogs in Example i using either 100 mg (0.2 mmol) $NiL^A_2(1,4-(CF_2)_4—)(L^A$ is $P(Et)_3$), 100 mg (0.2 mmol) $NiL^B_2(1,4-(CF_2)_4—)(L^B$ is $P(O-p-tol)_3)$, or 100 mg $NiL^B_2(1,4-(CF_2)_4—)$ and 10 mg (0.01 mmol) $RhCl(PPh_3)_3$. The vapor phase sample from $NiL^A_2$ $(1,4-(CF_2)_4—)$ indicated formation of H $(CF_2)_4$H and perfluorocyclobutene in a 1:2 ratio. The $^{19}$F NMR spectrum indicated the presence of $NiL^A_2$ $(1,4-(CF_2)_4—)$ (about 30%), $H(CF_2)_4H$ and perfluorocyclobutene. Vapor phase analysis of the $NiL^B_2$ $(1,4-(CF_2)_4—)$ experiments suggested $CFCL_2CF_2Cl$ contamination in both samples, air in the sample from the uncatalyzed reaction, and $CO_2$ in that from the catalyzed reaction. Nevertheless, no perfluorocyclobutene was observed in either case. The $^{19}$F NMR liquid phase analysis showed that the uncatalyzed reaction gave only ca. 25% conversion of $NiL^B_2(1,4-(CF_2)_4—)$, whereas the catalyzed reaction showed complete conversion; in both runs to $H(CF_2)_4H$. Several by-products which appeared to contain P-F bonds

TABLE I

| Run No. | Additives | % Conv. | Vapor Phase Anal. | | | Liquid Phase Anal. | | |
|---|---|---|---|---|---|---|---|---|
| | | | 338[1]/347[2] | 356s[3] | c-1316[4] | 338pcc[1] | 347pcc[2] | 356qcc[5] |
| 1 | Pd/Carbon | 16 | 88.5 | 9 | 2.5 | 4.5 | 80.5 | 15 |
| 2 | Rhodium/Carbon | 25 | 42.5 | — | 47.5 | 18 | 16 | 6 |
| 3 | None | 49 | 97.5 | — | 1.5 | 59.5 | 38 | — |
| 4 | $RhCl(PPh_3)_3$ | 100 | 72 | 6 | 15.5 | 4.5 | 78 | 17.5 |
| 5 | $RhCl(PPh_3)_3$ | 93 | 90.5 | 6.5 | 3 | 8.5 | 77 | 14.5 |
| 6 | $RuHCl(PPh_3)_3$ | 97.5 | 46.5 | 28.5 | 2 | 7 | 62 | 31 |
| 7 | $PPh_3$ | 84.5 | 90 | 6.5 | 3.5 | 13.5 | 71.5 | 15 |
| 8 | $RuHCl(PPh_3)_3$ | 100 | 92 | 3.5 | 2.5 | 3.5 | 90.5 | 6 |
| 9 | $RhCl(PPh_3)_3$ | 98 | 89 | 9.5 | 1 | 1 | 73.5 | 25.5 |
| 10 | $[Rh(COD)(DPPB)]BF_4$ | 88 | 86.5 | 0 | 12.5 | 37 | 63 | — |
| 11 | $RhCl(PPh_3)_3$ | 5 | 93.5 | 1.5 | 1.5 | 12.5 | 83.5 | 4 |
| 12 | $P(O-p-tol)_3$ | 15 | 96 | 0.5 | 0.5 | 64 | 26 | — |

[1]338 and 338pcc are $H(CF_2)_4H$
[2]347 and 347pcc are $H(CF_2)_3CFH_2$
[3]356s are isomers of $C_4H_4F_6$
[4]C-1316 is perfluorocyclobutene
[5]356qcc is $CH_2FCF_2CF_2CH_2F$ were also observed at ca. −30 ppm, but there was no indication of H(CF$_2$)$_3$CFH$_2$ or isomers of C$_4$H$_4$F$_6$.

Example 4

Preparation of (Diphite)Ni(1,4-CH$_2$CH$_2$CF$_2$CF$_2$—)

A solution of 0.53 g (Diphite)Ni(ethylene) in 13.05 g benzene was charged to a 50 cc Hastelloy™ C (nickel alloy) autoclave. TFE was admitted to a pressure of 267 kPa (24 psig), and the reaction stirred for 17.3 hours at 25° C. The solvent was removed in vacuo from a 4 mL portion of the product, and the solid residue was redissolved in deuterobenzene for NMR analysis. Phosphorus NMR indicated an approximate composition of 70% metallacycle and 30% (Diphite)$_2$Ni. The signal for (Diphite)Ni(ethylene), which would appear at about 170 ppm, was completely absent indicating complete conversion of the starting material. (Diphite)$_2$Ni was present in the starting material, so conversion of ethylene complex to metallacycle was quantitative. The $^{31}$P{$^1$H} NMR shows an AB pattern for the metallacycle: 154.2 (m, 1P), 158.3 (m, 1P), Unreacted (Diphite)$_2$Ni appears as a singlet at 164.8 ppm. The $^{19}$F{1H} approximates an ABXY pattern:. −92.0 (m, 2F, the "AB" part), −116.3 ("d", J$_{FF}$ about 235 Hz, "X"), −120.2 ("d", J$_{FF}$ about 235 Hz, "Y"). The location of the alpha fluorines around −90 to −100 ppm and the beta fluorines at around −120 ppm is characteristic of these fluorinated metallacyclopentanes, and distinguishes them from simple mono-TFE complexes and other possible structures.

Example 5

Hydrogenation of (Diphite)Ni(1,4-CH$_2$CH$_2$CF$_2$CF$_2$—)

The product from Example 4 (about 0.5 mmol) was dissolved in benzene and charged to a 50 cc autoclave. Hydrogen was admitted to 7000 kPa (1000 psig) and the autoclave was heated to 65° C. After 1 hour at 65° C., the autoclave was cooled, vented, and brought into the glovebox for sampling. NMR analysis showed the metallacycle to be completely hydrogenated. The major species observed by $^{31}$P NMR was (Diphite)$_2$Ni, 164.8 ppm (s). $^{19}$F NMR showed HCF$_2$CF$_2$CH$_2$CH$_3$: −118.5 (t, J$_{HF}$ was 18 Hz), −135.6 (d, J$_{HF}$ was 54 Hz). The $^{19}$F NMR spectrum was identical to HCF$_2$CF$_2$CH$_2$CH$_3$ formed in Example 7, which was positively identified by GC-MS.

Example 6

Preparation of (Diphite)Ni(1,4-CF$_2$CF$_2$CF$_2$CF$_2$—)

This compound was prepared by ligand exchange according to the equation

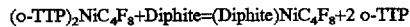

A solution of 0.037 mmol (o-TTP)$_2$Ni(1,4-CF$_2$CF$_2$CF$_2$CF$_2$—) in 3 g C$_6$D$_6$ was treated with 0.0435 mmol Diphite at 25° C. After 20 minutes, the $^{31}$P NMR spectrum showed a mixture of (Diphite)Ni(1,4-CF$_2$CF$_2$CF$_2$CF$_2$—) (143.06 ppm, m) and (o-TTP)$_2$Ni(1,4-CF$_2$CF$_2$CF$_2$CF$_2$—) (112.8 ppm, m) in the ratio 4.3:1. Free Diphite (147 ppm, s) and o-TTP (131.8 ppm, s) were also present in the expected amounts.

Example 7

Preparation of (o-TTP)$_2$Ni(1,4-CH$_2$CH$_2$CF$_2$CF$_2$—)

A solution of 0.775 g (o-TTP)$_2$Ni(ethylene) in 30.3 g benzene was charged to a 50 cc Hastelloy ™ C (nickel alloy) autoclave. TFE was admitted to a pressure of 267 kPa (24 psig), and the reaction mixture stirred for 1.5 hours at 25° C. Phosphorus NMR showed that the resonance due to (o-TTP)$_2$Ni(ethylene) at 143.4 ppm was now completely gone while major new signals appeared due to (o-TTP)$_2$Ni(1,4-CH$_2$CH$_2$CF$_2$CF$_2$—) (complex multiplets centered at 127.8 and 129.3 ppm). This is similar to the $^{31}$P NMR spectrum of (Diphite)Ni(1,4-CH$_2$CH$_2$CF$_2$CF$_2$—) described in Example 4. $^{19}$F{$^1$H}: −96.7 (m, 2F), −120.1 (m, 2F). This $^{19}$F NMR spectrum also shows the assymmetry of this complex—the alpha fluorines appear as an apparent doublet of doublets from coupling to two inequivalent o-TTP ligands. Smaller, incompletely resolved couplings are also present.

Example 8

Hydrogenation of (o-TTP)$_2$Ni(1,4-CH$_2$CH$_2$CF$_2$CF$_2$—)

The product from Example 7 above was treated with 7000 kPa (1000 psig) hydrogen at 24° C. for 17 hours. The products were analyzed by NMR and GC-MS. The normalized GC-MS results, excluding benzene solvent, showed 1% TFE, 22% HFC-134 (CF$_2$HCF$_2$H), and 77% HFC-374pc (CH$_3$CH$_2$CF$_2$CF$_2$H). The proton-coupled $^{19}$F NMR is consistent with this: −118.5 (t, J$_{HF}$ about 18 Hz, β fluorines of HFC-374), −135.6 (d, J$_{HF}$ about 54 Hz, terminal CF$_2$H group of HFC-374), −127.6 (t, J$_{PF}$ about 44 Hz, (o-TTP)$_2$Ni(TFE)), 136.8 (d, 55 Hz, HFC-134). Proton-fluorine couplings were distinguished from phosphorus-fluorine couplings by observing the proton-decoupled $^{19}$F NMR spectrum, wherein the signals at −118.5 and −135.6 collapsed to singlets, but the signal at -127.6 remained a triplet. The phosphorus NMR showed two major species: free o-TTP and probably (o-TTP)$_2$Ni(TFE). $^{31}$P{1H}: 129.4 (s, free o-TTP), 133.0 (quintet, J$_{PF}$ about 44 Hz, (o-TTP)$_2$Ni (TFE)).

Example 9

Preparation of HCF$_2$CF$_2$CF$_2$CF$_2$H

A. Preparation of (o-TTP)$_2$Ni(1,4-CF$_2$CF$_2$CF$_2$CF$_2$—)

A solution of 0.4596 g Ni(o-TTP)$_3$ and 0.4801 g o-TTP in 5 g benzene was charged to a 50 cc autoclave. TFE was admitted to a pressure of 308 kPa (30 psig) and the reaction mixture stirred at 24° C. for 16.5 hours. The $^{31}$P NMR showed that all Ni(o-TTP)$_3$ had been consumed. Free o-TTP and (o-TTP)$_2$Ni(1,4-CF$_2$CF$_2$CF$_2$CF$_2$—) were present in the expected integrated intensities of 4 and 2 respectively. The NMR data match that reported by Tolman et al. in *J. Am. Chem. Soc.*, Vol. 96, page 2774 (1974). Metallacycle appears as a quintet in the $^{31}$P NMR spectrum with 40 Hz splitting due to the four equivalent α fluorines of the perfluorometallacyclopentane ring, while the α fluorines appear as a triplet in the $^{19}$F NMR spectrum, with 40 Hz coupling to two equivalent o-TTP ligands. The β fluorines appear as a broad singlet—fluorine-fluorine coupling is apparently too small to be resolved in our $^{19}$F spectra. $^{31}$P{1H}: 131.5 (s, free o-TTP), 115.3 (quintet, J$_{PF}$ was 40 Hz, metallacycle). $^{19}$F{1H}: 97.1 (t, J$_{PF}$ was 40 Hz, α fluorines), 137.4 (s, β fluorines).

This reaction was repeated on a preparative scale. Thus a solution of 4.51 g (o-TTP)$_3$Ni in 26.43 g toluene was placed in an autoclave, pressurized with 343 kPa (35 psig) TFE, and allowed to stir for 18 hours. The solvent was removed in vacuo and the solid residue washed with 50 mL petroleum ether to remove free o-TTP. The solid was collected by filtration and dried, yielding 3.32 g pale yellow solid. The pet ether was reduced to about half its original volume, yielding an additional 0.11 g product. Total yield: 3.43 g, 88% based on Ni. The $^{31}$P and $^{19}$F NMR spectra were identical to those described above except free ligand was completely absent, having been removed in the workup.

B. Hydrogenation of (o-TTP)$_2$Ni(1,4-CF$_2$CF$_2$CF$_2$CF$_2$—)

The product from above was treated with 7000 kPa (1000 psig) hydrogen at 24° C. for 2 hours. No significant hydrogenation occurred. The same product was then treated with 7000 kPa (1000 psig) hydrogen at 65° C. for 1 hour, but again, no significant hydrogenation occurred. The same product was then treated with 7000 kPa (1000 psig) hydrogen at 100° C. for 1.5 hours. $^{19}$F NMR showed complete, clean conversion of the metallacycle to HFC-338pcc: −130.9 (s, β fluorines), −137.3 (d, α fluorines). The $^{31}$P NMR spectrum confirmed the absence of metallacycle, but the only major signal observed was that due to free o-TTP, suggesting that the metal complex decomposed. This was confirmed by observation of a precipitate of black, magnetic, nickel met a 1.

Example 10

Preparation of-(p-TTP)$_2$Ni(1,4-CF$_2$CF$_2$CF$_2$CF$_2$—)

A solution of 1.45 g (p-TTP)$_4$Ni and 0.861 g p-TTP in 27.94 g toluene was placed in an autoclave, pressurized with 343 kPa (35 psig) TFE, and heated to 75° C. After 1 hour, NMR showed that little reaction had occurred, so the temperature was increased to 100° C. After an additional 1.8 hour at 100° C., an integrated $^{31}$P NMR indicated 50% conversion of (p-TTP)$_4$Ni to (p-TTP)$_2$Ni(1,4-CF$_2$CF$_2$CF$_2$CF$_2$—). $^{31}$P{$^1$H}: 132.0 (s, (p-TTP)$_4$Ni), 129.0 (s, free p-TTP), 115.8 (broad, (p-TTP)$_2$Ni(1,4-CF$_2$CF$_2$CF$_2$CF$_2$—). $^{19}$F: −138.5 (s, beta fluorines), −98.8 (broad, alpha fluorines), −132.8 (s, dissolved TFE used as chemical shift secondary reference).

The product of this reaction was hydrogenated (see Example 12).

Example 11

Alternate preparation of (p-TTP)$_2$Ni(1,4-CF$_2$CF$_2$CF$_2$CF$_2$—)

This complex was also prepared by ligand exchange starting from (o-TTP)$_2$Ni(1,4-CF$_2$CF$_2$CF$_2$CF$_2$—). Thus, a solution of 0.1437 g (o-TTP)$_2$N(1,4-CF$_2$CF$_2$CF$_2$CF$_2$—) in 5.12 g toluene was treated with 0.105 g p-TTP. $^{31}$P NMR showed nearly complete displacement of the o-TTP by p-TTP, forming (p-TTP)$_2$Ni(1,4-CF$_2$CF$_2$CF$_2$CF$_2$—) as the predominant organometallic product.

$^{31}$P{$^1$H}: 131.4 (s, free o-TTP), 129.2 (s, free excess p-TTP), 115.7 (m, (p-TTP)$_2$Ni(1,4-CF$_2$CF$_2$CF$_2$CF$_2$—)).

Example 12

Hydrogenation of (p-TTP)$_2$Ni(1,4-CF$_2$CF$_2$CF$_2$CF$_2$—)

The crude reaction product from the metallacycle preparation described in Example 10 was pressurized with 7000 kPa (1000 psig) hydrogen and heated. After 1.5 h at 100° C., $^{31}$P NMR indicated that little hydrogenation had occurred—a large amount of metallacycle remained. The temperature was increased to 120° C. After an additional 1.5 hours, NMR indicated that approximately 70% of the metallacycle had been hydrogenated, forming HFC-338pcc and regenerating (p-TTP)$_4$Ni. These were the only species detected by $^{19}$F NMR.

Example 13

Preparation of HCF$_2$CF$_2$CF$_2$CF$_2$H

A. Preparation of Ni(P(n-Bu)$_3$)$_3$

A solution of 4.24 g P(n-Bu)$_3$ ("P") in 15 ml toluene was treated with 2.76 g (COD)$_2$Ni, sprinkled in over about 15 minutes. The mixture was hydrogenated with 790 kPa (100 psig) H$_2$ at 100° C. for 1 hour, after which time $^{31}$P NMR showed predominantly Ni"P"$_3$ and free "P", with the integrated intensity of Ni"P"$_3$ as expected based on the relative amounts of Ni and "P" used (4.5"P"/Ni). The solvent was removed in vacuo to dryness and the product used as is.

$^{31}$P{$^1$H}: −2.0 (broad s, Ni"P"$_3$, integral 3/4.5 of total P integral), −30 (broad, free P).

B. Preparation of (P(n-Bu)$_3$)$_2$Ni(1,4-CF$_2$CF$_2$CF$_2$CF$_2$—)

A solution of 1.217 g Ni(P(n-Bu)$_3$)$_3$ (see above) in 30.55 g toluene was treated with 343 kPa (35 psig) TFE at 25° C. for 1 hour. $^{31}$P NMR indicated clean, quantitative conversion of Ni"P"$_3$ to "P"$_2$Ni(1,4-CF$_2$CF$_2$CF$_2$CF$_2$—). $^{19}$F NMR matched the literature, confirming formation of metallacycle.

$^{31}$P{$^1$H}: 9.1 (quintet, J$_{PF}$ was 23 Hz). −31.0 (broad s, free P-nBu$_3$). No signal was observed near −2 ppm, where Ni"P"$_3$ would have appeared.

$^{19}$F: −138.8 (s, beta fluorines), −103.2 (t, J$_{PF}$ was 23 Hz, alpha fluorines), −132.8 (s, dissolved TFE, used as chem shift reference).

C. Hydrogenation of (P(n-Bu)$_3$)$_2$Ni(1,4-CF$_2$CF$_2$CF$_2$CF$_2$—)

The product from the above reaction, without isolation, was hydrogenated with 790 kPa (100 psig) H$_2$ for 1.5 hour at 100° C., then 0.5 hour at 120° C. $^{19}$F NMR indicated approx 80% conversion of metallacycle to CHF$_2$CF$_2$CF$_2$CHF$_2$ (HFC-338pcc).

Bu$_3$PF$_2$ was detected in both the $^{31}$P and $^{19}$F NMR. $^{31}$P{$^1$H}: −13 (t, J$_{PF}$ about 490 Hz). $^{19}$F: −34.2 (doublet of multiplets, J$_{PF}$ about 490 Hz).

Example 14

Preparation of HCF$_2$CF$_2$CF$_2$CF$_2$H

A. Preparation of (monophite)$_2$Ni(1,4-CF$_2$CF$_2$CF$_2$CF$_2$—)

A solution of 1.6293 g (monophite)$_4$Ni in 30.345 g toluene was treated with 308–377 kPa (30–40 psig).TFE and heated at 65° C. for a total of 68 hours. An integrated $^{31}$P NMR spectrum indicated 56% conversion of (monophite)$_4$Ni to (monophite)$_2$Ni(1,4-CF$_2$CF$_2$CF$_2$CF$_2$—).

$^{31}$P{$^1$H}: 142.3 (quintet, J$_{PF}$ was 41 Hz, (monophite)$_2$Ni (1,4-CF$_2$CF$_2$CF$_2$CF$_2$—)), 146.6 (s, free monophite), 163.8 (s, (monophite)$_4$Ni).

B. Hydrogenation of (monophite)$_2$Ni(1,4-CF$_2$CF$_2$CF$_2$CF$_2$—)

The product from the above reaction, without isolation, was treated with 7000 kPa (1000 psig) H$_2$ and heated to 120° C. for 3 hours. $^{31}$P and $^{19}$F NMR showed that the metallacycle had been hydrogenated; producing HFC-338pcc as the major organic product and regenerating (monophite)$_4$Ni as the major organometallic product.

Example 15

Preparation of (TIPP)$_2$Ni(1,4-CF$_2$CF$_2$CF$_2$CF$_2$—)

A. Preparation of Ni(TIPP)$_4$

Ni(COD)$_2$ (3.01 g, 11 mmol) was added to a solution of TIPP (10.49 g, 50 mmol) in 30 mL petroleum ether. The resulting mixture was stirred for 30 minutes, then the pet ether was removed in vacuo, leaving a white solid. The product was washed with 20 mL methanol, then dried in vacuo yielding Ni(TIPP)$_4$ (9.89 g, 11 mmol, 100% yield), which was pure by NMR spectroscopy. 31P{$^1$H}: 155.5 ppm (s), 1H: 4.89 (q), 1.36 (d).

B. Alternate preparation of Ni(TIPP)$_4$ from NiBr$_2$(THF)$_x$

NiBr$_2$(THF)$_x$ was prepared by treatment of 1 g Ni powder (INCO type 123) suspended in 100 mL THF with 2.45 g Br$_2$. The resulting orange solid was collected on a filter and rinsed with 2 to 3 mL ether, then dried under a stream of nitrogen to give 4.76 g of product. NiBr$_2$(THF)$_x$ is a relatively soluble nickel halide, which facilitates subsequent reactions in comparison to anhydrous nickel halides, which are quite insoluble and slow to react.

A mixture of 0.5142 g NiBr$_2$(THF)$_x$ and 1.5630 g TIPP in 3 to 4 mL THF was treated with 0.8138 g Zn powder at 25° C. After 5 minutes, the characteristic purple color of NiBr$_2$(TIPP)$_x$ faded. A $^{31}$P NMR sample was taken after 30 minutes, and showed complete conversion to Ni(TIPP)$_4$.

C. Alternate preparation of Ni(TIPP)$_4$ from anhydrous NiCL$_2$ in THF

A mixture of 0.1648 g NiCL$_2$ powder, 1.6356 g TIPP, and 0.8210 g Zn powder in 7 mL THF was heated to 60° C. in a Fisher-Porter tube. After 3 hours, approx 10% of the TIPP was converted to Ni(TIPP)$_4$. The temperature was increased to 80° C. After an additional 20 h, $^{31}$P NMR indicated that the reaction had reached completion, forming Ni(TIPP)$_4$. The elevated temperatures required in this preparation compared to the preceding one reflect the lower reactivity of anhydrous NiCL$_2$ vs NiBr$_2$(THF)$_x$.

D. Alternate preparation of Ni(TIPP)$_4$ from anhydrous NiCL$_2$ in toluene

A mixture of 0.1657 g NiCL$_2$, 1.68 g TIPP, and 0.8729 g Zn powder in 4 mL toluene was heated in a Fisher-Porter tube to 80° C. for 17.5 hours. $^{31}$P NMR showed a trace of Ni(TIPP)$_4$ ($\leq$5% conversion). The temperature was increased to 110° C. After an additional 23 hours, $^{31}$P NMR showed that free TIPP was gone, with Ni(TIPP)$_4$ being the major organometallic product. The more extreme conditions required in this preparation compared to the preceding one reflect the lower solubility/reactivity of NiCL$_2$ in toluene compared to THF.

E. Preparation of (TIPP)$_2$Ni(1,4-CF$_2$CF$_2$CF$_2$CF$_2$—)

A solution of Ni(TIPP)$_4$ (9.12 g, 10.22 mmol) and TIPP (4.33 g, 20.8 mmol) in toluene (22.1 g) was charged to a 50 cc autoclave, heated to 60° C., and reacted with 170 kPa (10 psig) TFE gas for 2 hours. The autoclave was cooled, and the product isolated by removal of solvent in vacuo. After washing with 10 mL petroleum ether to remove free TIPP, the yellow solid was dried to yield 5.10 g. Slow evaporation of the pet ether rinse yielded a second crop weighing 1.48 g. Total yield: 6.58 g (95%).

The identity of this new compound was established by x-ray crystallography.

$^{31}$P{$^1$H}: 125.3 ppm (quintet, J$_{PF}$ was 38 Hz). At high concentrations and in the presence of excess TIPP, this often appears as a broad singlet due to TIPP exchange.

$^{19}$F: −138.2 (s, β fluorines), −102.2 (t, J$_{PF}$ was 38 Hz, α fluorines, sometimes appears as a broad singlet as noted above).

F. Reaction of Ni(TIPP)$_4$ with TFE at 110° C.

A solution of 5.3 g Ni(TIPP)$_4$ and 2.51 g TIPP in 14.38 g toluene was heated under an inert atmosphere of helium to 110° C. and stirred at 1500 rpm. When the temperature stabilized, TFE was admitted at a constant pressure of 308 kPa (30 psig) and the uptake monitored by recording pressure drop in a supply cylinder of known volume (1143 cc). TFE uptake was complete in approximately 3 minutes. TFE uptake was linear with time (zero-order) and occurred at a rate comparable to the rate of TFE dissolution.

$^{31}$P and $^{19}$F NMR of the product solution confirmed clean, quantitative formation of (TIPP)$_2$Ni(1,4-CF$_2$CF$_2$CF$_2$CF$_2$—), with the expected release of 2 TIPP from Ni(TIPP)$_4$ starting material.

Example 16

Hydrogenation of (TIPP)$_2$Ni(1,4-CF$_2$CF$_2$CF$_2$CF$_2$—) to HFC-338pcc with regeneration of Ni(TIPP)$_4$ A solution of 0.7343 g (TIPP)$_2$Ni(1,4-CF$_2$CF$_2$CF$_2$CF$_2$—) (described above in Example 15E) and 0.97 g TIPP in 28.8 g toluene was hydrogenated with 7000 kPa (1000 psig) H$_2$ for 1 hour at 100° C. An integrated NMR spectrum showed that the metallacycle was completely hydrogenated and that Ni(TIPP)$_4$ had been reformed as the main organometallic product.

Of special note, there were no signs of decomposition to Ni metal, as was observed with (o-TTP)$_2$Ni(1,4-CF$_2$CF$_2$CF$_2$CF$_2$—) described above in Example 9B.

Example 17

Reaction of recycled Ni(TIPP)$_4$ with TFE, reforming (TIPP)$_2$Ni(1,4-CF$_2$CF$_2$CF$_2$CF$_2$—)

The product solution from Example 16 was treated with 274 kPa (25 psig) TFE for 30 minutes at 65° to 70° C. A $^{31}$P NMR spectrum indicated complete conversion of Ni(TIPP)$_4$ to (TIPP)$_2$Ni(1,4-CF$_2$CF$_2$CF$_2$CF$_2$—).

Example 18

Hydrogenation of (TIPP)$_2$Ni(1,4-CF$_2$CF$_2$CF$_2$CF$_2$—)

A solution of 8.91 g Ni(TIPP)$_4$ and 4.18 g TIPP in 21.84 g toluene was treated with 239–308 kPa (20–30 psig) TFE and heated to 65° C. over about 30 minutes, then immediately cooled. $^{31}$P NMR showed complete conversion of Ni(TIPP)$_4$ to (TIPP)$_2$Ni(1,4-CF$_2$CF$_2$CF$_2$CF$_2$—).

This solution was heated under helium to 160° C. When the temperature had stabilized, 2066 kPa (285 psig) hydrogen was admitted and allowed to react for 30 minutes. The reactor was cooled rapidly, over 8 minutes, back to ambient temperature. $^{31}$P and $^{19}$F NMR both indicated 95–97% conversion of the metallacycle to HFC-338pcc and Ni(TIPP)$_4$. No significant fluorinated or P-containing side-products were detected.

Example 19

Synthesis of HFC-338pcc using Ni(TIPP)$_4$ with 2 moles of excess TIPP/Ni

Recycle of metal complex

A solution of 8.963 g Ni(TIPP)$_4$ and 4.226 g TIPP in 21.5 g toluene was treated with 274 kPa (25 psig) TFE at 25°–30° C. for 3.5 hours. $^{31}$P NMR indicated 96% conversion of Ni(TIPP)$_4$ to (TIPP)$_2$Ni(1,4-CF$_2$CF$_2$CF$_2$CF$_2$—).

The resulting solution was hydrogenated with 7000 kPa (1000 psig) hydrogen for 8.5 hours at 100° C. $^{31}$P and $^{19}$F NMR indicated about 85% hydrogenation of metallacycle, forming HFC-338pcc and regenerating Ni(TIPP)$_4$.

The TFE reaction-hydrogenation sequence was repeated twice more. The reactor contents were transferred to a simple distillation apparatus and heated with an oil bath. The apparatus consisted of a pot, head and condenser, but no distillation column, to simulate minimal rectification as in a simple single-stage flash. The product distilled over at a head temperature of 40° to 46° C., with the bath temperature reaching 125° C.

The product was analyzed by GC-MS and the pot contents by $^{31}$P NMR. The GC-MS analysis of the distillate revealed a mixture of HFC-338pcc and toluene in approximately equal amounts, along with a trace of deuterobenzene which had been used in nmr samples. No significant fluorinated impurities were detected. $^{31}$P NMR analysis of the pot contents showed 85% Ni(TIPP)$_4$ and 15% (TIPP)$_2$Ni(1,4-CF$_2$CF$_2$CF$_2$CF$_2$—), as well as free TIPP. Small amounts of phosphorus-containing impurities were visible in the P NMR (signals at −2 and +5 ppm), which were present in the initial metal complex before its first use and did not increase over the course of the three turnovers. The relative amounts of nickel species did not change as a result of the distillation. Taken together, this information indicates that Ni(TIPP)$_4$ is recyclable.

Example 20

Synthesis of HFC-338pcc using Ni(TIPP)$_4$ with a large excess of TIPP

A solution of 9.71 g Ni(TIPP)$_4$ and 50 g TIPP in 10 g benzene was reacted with 308 kPa (30 psig) TFE at 65° C. for 2 hours. $^{31}$P NMR clearly showed that the Ni(TIPP)$_4$ was completely converted to (TIPP)$_2$Ni(1,4-CF$_2$CF$_2$CF$_2$CF$_2$—).

This solution was treated with 7000 kPa (1000 psig) hydrogen at 100° C. for 8 hours. NMR showed that the metallacycle had hydrogenated completely, producing HFC-338pcc (identified by $^{19}$F NMR) and Ni(TIPP)$_4$ (identified by $^{31}$P NMR).

Another exposure to 274 kPa (25 psig) TFE at 65° C. regenerated metallacycle. Hydrogenation at 7000 kPa (1000 psig) and 100° C. produced more HFC-338pcc and regenerated Ni(TIPP)$_4$.

Clearly, neither excess TIPP nor the presence of HFC-338pcc from previous reactions prevents formation and hydrogenation of metallacycle.

Example 21

One-pot HFC-338pcc synthesis at 100° C.

A solution of 0.147 g Ni(TIPP)$_4$ in 20 ml toluene was charged to a 75 cc shaker tube. The tube was pressurized with 791 kPa (100 psig) TFE, then 1480 kPa (200 psig) H$_2$, making a total pressure of 2170 kPa (300 psig). The reactor was closed, heated to 100° C., and shaken at that temperature for 21 hours. After cooling, the pressure was vented. Gas samples were taken when the pressure was 791 kPa (100 psig), and again at approx 136 kPa (5 psi) and analyzed by GC-MS. The results are shown below:

| Component (Percent) | 136 kPa (5 psi) | 791 kPa (100 psi) |
| --- | --- | --- |
| TFE | 97.8 | 98.3 |
| 134 (CF$_2$HCF$_2$H) | trace | trace |
| 218 (C$_3$F$_8$) | 0.01 | 0.04 |
| C-318 (cyclo-C$_4$F$_8$) | 1.67 | 1.34 |
| 338pcc (CHF$_2$CF$_2$CF$_2$CHF$_2$) | 0.43 | 0.26 |

The liquid contents of the reactor were analyzed directly by NMR. $^{31}$P NMR showed the nickel to be present as metallacycle complex, (TIPP)$_2$Ni(1,4-CF$_2$CF$_2$CF$_2$CF$_2$—). Since we started with Ni(TIPP)$_4$, $^{31}$P NMR also showed the expected 2 moles of free TIPP per mole of metallacycle complex. The $^{19}$F NMR showed metallacycle along with an approximately equal molar amount of HFC-338pcc, indicating one turnover. $^{19}$F NMR also showed about 1 mole TFE/mole HFC-338pcc and a trace of perfluorocyclobutane.

Example 22

One-pot HFC-338pcc synthesis at 160° C.

The preceding example was repeated, except that the reaction was shaken at 160° C. for 17 hours. After cooling, the pressure was vented, and gas samples were taken at 791 kPa (100 psig) and 136 kPa (5 psig) and analyzed by GC-MS as before. The results are given below.

| Component (Percent) | 136 kPa (5 psi) | 791 kPa (100 psi) |
| --- | --- | --- |
| TFE | 65.52 | 65.95 |
| 134a (CF$_3$CFH$_2$) | 0.17 | 0.15 |
| C$_3$H$_6$ | 6.24 | 5.15 |
| 1216 (CF$_3$CF=CF$_2$) | 0.5 | 0.49 |
| 236ca (CHF$_2$CF$_2$CHF$_2$) | 0.04 | 0.03 |
| 218 (C$_3$F$_8$) | trace | trace |
| C-318 (cyclo-C$_4$F$_8$) | 25.87 | 26.52 |
| 338pcc (CHF$_2$CF$_2$CF$_2$CHF$_2$) | 1.54 | 1.09 |
| toluene |  | 0.55 |

The liquid contents of the reactor were analyzed by NMR. The $^{19}$F NMR, using a known amount of C$_6$F$_6$ as internal standard, showed formation of 0.707 mmol 338pcc, indicating 4.3 turnovers. $^{19}$F NMR also showed about 0.1 mole TFE/mole HFC-338pcc and about 0.05 mole perfluorocyclobutane/mole HFC-338pcc.

Example 23

Preparation of (TIPP)$_2$Ni(1,4-CH$_2$CH$_2$CF$_2$CF$_2$—)

A solution of 4.53 g Ni(TIPP)$_4$ in 14.22 g toluene was treated with a mixture of 138 kPa (20 psia) TFE and kPa (90 psia) ethylene at 25° to 30° C. for 17 hours. $^{31}$P NMR indicated 80% conversion of Ni(TIPP)$_4$ to a mixture of 2 parts (TIPP)$_2$Ni(1,4-CH$_2$CH$_2$CF$_2$CF$_2$—) and 1 part (TIPP)$_2$Ni(1,4-CF$_2$CF$_2$CF$_2$CF$_2$—).

31P{$^1$H}: 13.6 (br m, (TIPP)$_2$Ni(1,4-CH$_2$CH$_2$CF$_2$CF$_2$—)), 213.8 (br m, TIPP)$_2$Ni (1,4-CF$_2$CF$_2$CF$_2$CF$_2$—)), 139.3 (s, free TIPP), 154.7 (s, Ni(TIPP)$_4$). $^{19}$F: −100.2 (br, alpha-fluorines on (TIPP)$_2$Ni (1,4-CH$_2$CH$_2$CF$_2$CF$_2$—)), −119.6 (m, beta-fluorines on (TIPP)$_2$Ni(1,4-CH$_2$CH$_2$CF$_2$CF$_2$—)), −102.2 (br, alpha-fluorines on (TIPP)$_2$Ni(1,4-CF$_2$CF$_2$CF$_2$CF$_2$—)), −138.2 (br, beta-fluorines on (TIPP)$_2$Ni(1,4-CF$_2$CF$_2$CF$_2$CF$_2$—)).

The resulting solution was hydrogenated with 2170 kPa (300 psig) hydrogen for 1 hour at 150° C. and $^{19}$F NMR indicated complete hydrogenation of both metallacycles, forming a mixture of 35% $HCF_2CF_2CF_2CF_2H$ (HFC-338pcc) and 65% $HCH_2CH_2CF_2CF_2H$ (HFC-374), and regenerating $Ni(TIPP)_4$. The product composition determined by NMR was confirmed by GC-MS, which showed 57% HFC-374, 25% HFC-338pcc, 10% ethane, and 7% propane (excluding toluene solvent).

What is claimed is:

1. A compound of the formula $L_2Ni(1,4-CR^1_2CR^1_2CR^2_2CR^2_2-)$ wherein each $R^1$ is independently selected from the group consisting of H, F, Cl, CN, R, OR, $CO_2R$, $C(O)R$, $OC(O)R$, $R^f$, $OR^f$, $CO_2R^f$, $C(O)R^f$ and $OC(O)R^f$, where R is a hydrocarbyl group and $R^f$ is a $C_1$ to $C_{10}$ polyfluoroalkyl group, provided that at least one $R^1$ is F, wherein each $R^2$ is independently selected from the group consisting of group H, F, Cl, CN, R, OR, $CO_2R$, $C(O)R$, $OC(O)R$, $R^f$, $OR^f$, $CO_2R^f$, $C(O)R^f$, $OC(O)R^f$ and difunctional linkages where an $R^2$ on each of two adjacent carbon atoms together form a link selected from the group consisting of $-CH_2CH_2CH_2-$, $-CH_2CH_2CH_2CH_2-$, $-CH_2CH_2CH(CH_3)-$, $-CH_2CH(CH_3)CH_2-$, $-C(O)OC(O)-$, and norborndiyl, and wherein each L is a ligand selected from the group consisting of (1) Group 14 ligands selected from the group consisting of CO, $\eta^2$ olefinic ligands, $\eta^2$ alkyne ligands, $\eta^5$-$C_5R''_5$ ligands where R" is hydrocarbyl or hydrogen, and $\eta^3$-$C_3R''_3$ ligands (2) Group 15 ligands selected from the group consisting of pyridine, picoline, 2,2'-bipyridine, ethylene diamine, hydrocarbyl nitriles, mono-, bi-, and polydentate anionic ligands, mono- and bidentate ligands of the formula $E^1(R^3)_3$ or $(R^3)_2E^1R'E^1(R^3)_2$ wherein $E^1$ is selected from the group consisting of N, P, As, Sb, and Bi, $R^3$ is selected from the group consisting of H, OR, OH, $NH_2$, NHR and $NR_2$ where each R is a hydrocarbyl group and R' is an ether, alkylene, or arylene link between $E^1$ atoms, said $R^1$ optionally incorporating a pendant functional group selected from OR, OH, $NH_2$, NHR and $NR_2$ and two or more of said R, $R^3$ or R and $R^3$ groups optionally being cojoined and (3) Group 16 ligands, provided that when each L is a Group 15 ligand, and each $R^1$ and $R^2$ is F, then L is not trimethylphosphite, tri-o-tolylphosphite, triethylphosphine, tributylphosphine, methyldiphenyl phosphine, triphenylphosphine, dimethylphenyl arsine, 4-methylpyridine, dimethylarsine, 2,2-bipyridyl, or 1,2-bis(diphenyl phosphino)ethane, and provided that when three $R^1$ groups and three $R^2$ groups are F and the remaining $R^1$ group and $R^2$ group are H, then L is not triphenylphosphine or methydiphenylphosphine.

2. The compound of claim 1 selected from the group consisting of $L_2Ni(1,4-CF_2CF_2CH_2CH_2-)$, $L_2Ni(1,4-CF_2CH_2CH_2CF_2-)$, $L_2Ni(1,4-CH_2CF_2CF_2CH_2-)$, $L_2Ni(1,4-CF_2CH_2CF_2CH_2-)$, $L_2Ni(1,4-CClFCF_2CClFCF_2-)$, $L_2Ni(1,4-CClFCF_2CF_2CClF-)$, $L_2Ni(1,4-CF_2CClFCClFCF_2-)$, $L_2Ni(1,4-(CF_3O)CFCF_2CF_2CF(OCF_3)-)$, $L_2Ni(1,4-CF_2CF(OCF_3)CF_2CF(OCF_3)-)$, $L_2Ni(1,4-CF_2CF(OCF_3)CF(OCF_3)CF_2-)$, $L_2Ni(1,4-C(CN)FCF_2CF_2CF(CN)-)$, $L_2Ni(1,4-CF_2CF(CN)CF_2CF(CN)-)$, $L_2Ni(1,4-CF_2CF(CN)CF(CN)CF_2-)$, $L_2Ni(1,4-CHFCH_2CF_2CF_2-)$, $L_2Ni(1,4-CH_2CHFCF_2CF_2-)$, $L_2Ni(1,4-CH_2CHFCHFCF_2-)$, $L_2Ni(1,4-CHFCH_2CHFCF_2-)$, $L_2Ni(1,4-CHFCH_2CF_2CFH-)$, $L_2Ni(1,4-CH_2CHFCF_2CHF-)$, $L_2Ni(1,4-CH_2CH_2CClFCF_2-)$, $L_2Ni(1,4-CH_2CH_2CF_2CClF-)$, $L_2Ni(1,4-CHFCH_2CClFCF_2-)$, $L_2Ni(1,4-CH_2CHFCClFCF_2-)$, $L_2Ni(1,4-CHFCH_2CF_2CClF-)$, $L_2Ni(1,4-CH_2CHFCF_2CClF-)$, $L_2Ni(1,4-CH_2CH_2CF(OCF_3)CF_2-)$, $L_2Ni(1,4-CH_2CH_2CF_2CF(OCF_3)-)$, $L_2Ni(1,4-CHFCH_2CF(OCF_3)CF_2-)$, $L_2Ni(1,4-CH_2CHFCF(OCF_3)CF_2-)$, $L_2Ni(1,4-CHFCH_2CF_2CF(OCF_3)-)$, $L_2Ni(1,4-CH_2CHFCF_2CF(OCF_3)-)$, $L_2Ni(1,4-CHClCH_2CClFCF_2-)$, $L_2Ni(1,4-CH_2CHClCClFCF_2-)$, $L_2Ni(1,4-CHClCH_2CF_2CClF-)$, $L_2Ni(1,4-CH_2CHClCF_2CClF-)$, $L_2Ni(1,4-CHClCH_2CF_2CF_2-)$, $L_2Ni(1,4-CH_2CHClCF_2CF_2-)$, $L_2Ni(1,4-CH_2CHClCHFCF_2-)$, $L_2Ni(1,4-CHClCH_2CHFCF_2-)$, $L_2Ni(1,4-CHClCH_2CF_2CHF-)$, $L_2Ni(1,4-CH_2CHClCF_2CHF-)$, $L_2Ni(1,4-CHClCH_2CF(OCF_3)CF_2-)$, $L_2Ni(1,4-CH_2CHClCF(OCF_3)CF_2-)$, $L_2Ni(1,4-CHClCH_2CF_2CHF(OCF_3)-)$, $L_2Ni(1,4-CH_2CHClCF_2CF(OCF_3)-)$, $L_2Ni(1,4-CH_2CH(CN)CF_2CF_2-)$, $L_2Ni(1,4-CH(CN)CH_2CF_2CF_2-)$, $L_2Ni(1,4-CH_2CH(CO_2CH_3)CF_2CF_2-)$, $L_2Ni(1,4-CH(CO_2CH_3)CH_2CF_2CF_2-)$, $L_2Ni(1,4-(C_6H_5)CHCH_2CF_2CF_2-)$, $L_2Ni(1,4-CH_2CH(C_6H_5)CF_2CF_2-)$, $L_2Ni(1,4-(CF_3)CHCH_2CF_2CF_2-)$, $L_2Ni(1,4-CH_2CH(CF_3)CF_2CF_2-)$, $L_2Ni(1,4-CH(CN)CH(CN)CF_2CF_2-)$,

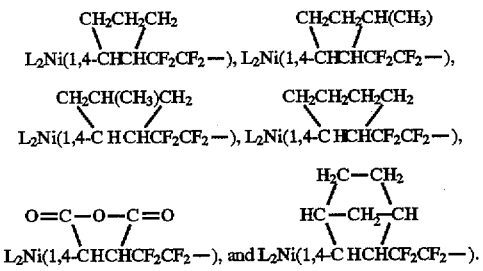

3. A compound of claim 1 wherein at least three $R^1$ groups are F and at least one $R^2$ group is not F.

4. A compound of claim 3 having the formula $L_2Ni(1,4-CFR^1CFR^1CHR^2CHR^2-)$ where each $R^1$ is selected from the group consisting of H, Cl, F, $OCF_3$ and CN, provided that at least one $R^1$ is F.

5. A compound of claim 3 wherein each $R^2$ is selected from the group consisting of H, Cl, F, CN, $CF_3$, $C_6H_5$ and $CO_2CH_3$, provided that at least one $R^2$ is H.

6. A compound of claim 3 wherein each $R^1$ and $R^2$ is F, provided that one $R^2$ group is not F.

7. A compound of claim 1 having the formula $L_2Ni(1,4-CFR^1CFR^1CHR^2CHR^2-)$ wherein each $R^1$ is selected from the group consisting of H, Cl, F, $OCF_3$ and CN, provided that at least one $R^1$ is F, and where each $R^2$ is CN or both $R^2$s together comprise a link selected from the group $-CH_2CH_2CH_2-$, $-CH_2CH_2CH_2CH_2-$, $-CH_2CH_2CH(CH_3)-$, $-CH_2CH(CH_3)CH_2-$, $-C(O)OC(O)-$, and norborndiyl.

8. A compound of claim 1 having the formula (Diphite)Ni(1,4-$CH_2CH_2CF_2CF_2-$)

wherein Diphite is
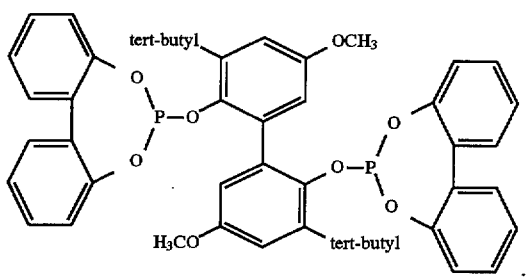
9. A compound of claim 1 having the formula
(TIPP)$_2$Ni(1,4-CF$_2$CF$_2$CF$_2$CF$_2$—)
wherein TIPP is tri-isopropyl phosphite.
10. A compound of claim 1 having the formula
L$_2$Ni(1,4-CClFCF$_2$CF$_2$CClF—).
11. A compound of claim 10 wherein L is a Group 15 ligand.
12. A compound of claim 11 wherein L is tri-isopropyl phosphite.
* * * * *